US009968553B1

(12) United States Patent
Rajewski et al.

(10) Patent No.: US 9,968,553 B1
(45) Date of Patent: *May 15, 2018

(54) ENALAPRIL COMPOSITIONS

(71) Applicants: Silvergate Pharmaceuticals, Inc., Greenwood Village, CO (US); University of Kansas, Lawrence, KS (US)

(72) Inventors: Lian G. Rajewski, Lawrence, KS (US); Roger A. Rajewski, Lawrence, KS (US); John L. Haslam, Lawrence, KS (US); Kathleen Heppert, Lawrence, KS (US); Michael C. Beckloff, Leawood, KS (US); Frank Segrave, Dublin, OH (US); Robert Mauro, Miller Place, NY (US); Peter Colabuono, Las Vegas, NV (US)

(73) Assignees: SILVERGATE PHARMACAUTICALS, INC., Greenwood Village, CO (US); UNIVERSITY OF KANSAS, Lawrence, KS (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/850,732

(22) Filed: Dec. 21, 2017

Related U.S. Application Data

(63) Continuation of application No. 15/433,743, filed on Feb. 15, 2017, now Pat. No. 9,855,214, which is a continuation of application No. 14/433,502, filed as application No. PCT/US2013/063096 on Oct. 2, 2013, now abandoned, which is a continuation of application No. 13/914,452, filed on Jun. 10, 2013, now Pat. No. 8,778,366, which is a continuation of application No. 13/670,355, filed on Nov. 6, 2012, now Pat. No. 8,568,747.

(60) Provisional application No. 61/710,489, filed on Oct. 5, 2012.

(51) Int. Cl.
*A61K 38/05* (2006.01)
*A61K 9/00* (2006.01)
*A61K 9/14* (2006.01)

(52) U.S. Cl.
CPC .......... *A61K 9/0095* (2013.01); *A61K 9/0053* (2013.01); *A61K 9/143* (2013.01); *A61K 9/145* (2013.01); *A61K 38/05* (2013.01)

(58) Field of Classification Search
None
See application file for complete search history.

(56) References Cited

U.S. PATENT DOCUMENTS

| | | | |
|---|---|---|---|
| 4,374,829 A | 2/1983 | Harris et al. |
| 4,472,380 A | 9/1984 | Harris et al. |
| 4,510,083 A | 4/1985 | Blacklock et al. |
| 4,743,450 A | 5/1988 | Harris et al. |
| 4,793,998 A | 12/1988 | Murthy et al. |
| 4,830,853 A | 5/1989 | Murthy et al. |
| 4,931,430 A | 6/1990 | Sudilovsky et al. |
| 5,049,553 A | 9/1991 | Sudilovsky |
| 5,698,562 A | 12/1997 | Mendes et al. |
| 6,028,222 A | 2/2000 | Dietlin et al. |
| 6,300,361 B1 | 10/2001 | Vivilecchia et al. |
| 6,300,362 B1 | 10/2001 | Vivilecchia et al. |
| 6,413,988 B1 | 7/2002 | De Proost |
| 6,509,350 B2 | 1/2003 | Vivilecchia et al. |
| 6,790,861 B2 | 9/2004 | Vivilecchia et al. |
| 6,869,963 B2 | 3/2005 | Patel et al. |
| 6,977,257 B2 | 12/2005 | Parab et al. |
| 7,101,888 B2 | 9/2006 | Reo et al. |
| 7,605,148 B2 | 10/2009 | Batta et al. |
| 8,153,824 B2 | 4/2012 | Sesha |
| 8,568,747 B1 | 10/2013 | Rajewski et al. |
| 8,778,366 B2 | 7/2014 | Rajewski et al. |
| 8,927,028 B2 | 1/2015 | Grenier et al. |
| 9,463,183 B1 | 10/2016 | Mosher et al. |
| 9,669,008 B1 | 6/2017 | Mosher et al. |
| 2004/0171669 A1 | 9/2004 | Chenevier |
| 2004/0258757 A1 | 12/2004 | Bosch et al. |
| 2006/0094760 A1 | 5/2006 | Fawzy et al. |
| 2006/0121066 A1 | 6/2006 | Jaeger et al. |
| 2007/0265344 A1 | 11/2007 | Strobel et al. |
| 2008/0221156 A1 | 9/2008 | Spireas |
| 2008/0234291 A1 | 9/2008 | Francois et al. |
| 2009/0206287 A1 | 8/2009 | Trupke et al. |
| 2009/0269287 A1 | 10/2009 | Berta |
| 2010/0222334 A1 | 9/2010 | Talamonti et al. |
| 2011/0003798 A1 | 1/2011 | Okram et al. |

(Continued)

FOREIGN PATENT DOCUMENTS

CA  1275350 C  10/1990
EP  2903690 A1  8/2015

(Continued)

OTHER PUBLICATIONS

AAPS American Association of Pharmaceutical Scientists, Preliminary Program, 2011 AAPS Annual Meeting and Exposition, Washington, D.C., Oct. 23-27, 2011, 112 pages.
Ahlin et al., "Investigation of polymeric nanoparticles as carriers of enalaprilat for oral administration," Int'l. Journ. Pharmaceutics, 239:113-120 (2002).
Allen et al., "Stability of alprazolam, chloroquine phosphate, cisapride, enalapril maleate, and hydralazine hydrochloride in extemporaneously compounded oral liquids," Am J. Health-Syst Pharm, 55:1915-1920 (1998).
Allen, Lisinopril 1 mg/mL oral liquid US Pharm., 38(2):36-37 (2013).
Al-Omari et al. "Effect of the drug-matrix on the stability of enalapril maleate in tablet formulations" Journal of Pharmaceutical and Biomedical Analysis, 25:893-902 (2001).

(Continued)

*Primary Examiner* — Samantha L Shterengarts
(74) *Attorney, Agent, or Firm* — Wilson Sonsini Goodrich & Rosati

(57) ABSTRACT

Provided herein are stable enalapril powder compositions for oral liquid formulation. Also provided herein are methods of using enalapril oral liquid formulations for the treatment of certain diseases including hypertension, heart failure and asymptomatic left ventricular dysfunction.

30 Claims, 3 Drawing Sheets

(56) References Cited

U.S. PATENT DOCUMENTS

| | | | |
|---|---|---|---|
| 2014/0100260 A1 | 4/2014 | Rajewski et al. | |
| 2015/0148335 A1 | 5/2015 | Bova et al. | |
| 2015/0258027 A1 | 9/2015 | Rajewski et al. | |
| 2017/0181968 A1 | 6/2017 | Rajewski et al. | |
| 2017/0266159 A1 | 9/2017 | Mosher et al. | |

FOREIGN PATENT DOCUMENTS

| | | | |
|---|---|---|---|
| WO | WO-9814196 A1 | 4/1998 | |
| WO | WO-9930690 A1 | 6/1999 | |
| WO | WO-0145667 A2 | 6/2001 | |
| WO | WO-02089775 A1 | 11/2002 | |
| WO | WO-2007070843 A2 | 6/2007 | |
| WO | WO-2009116078 A2 | 9/2009 | |
| WO | WO-2011031462 A2 | 3/2011 | |
| WO | WO-2011128783 A2 | 10/2011 | |
| WO | WO-2012085249 A2 | 6/2012 | |
| WO | WO-2014055667 A1 | 4/2014 | |
| WO | WO-2014178065 A1 | 11/2014 | |
| WO | WO-2017161339 A1 | 9/2017 | |

OTHER PUBLICATIONS

Bhardwaj et al., "Study of forced degradation behavior of enalapril maleate by LC and LC-MS and development of a validated stability-indicating assay method," Journal Pharmac. and Biomed. Analysis, 46:113-120 (2008).

Blowey. Update on the pharmacologic treatment of hypertension in pediatrics. Journal of Clinical Hypertension, 14(6):383-387 (2012).

Boukarim et al., Preservatives in liquid pharmaceutical preparations. The Journal of Applied Research, 9(1 & 2):14-17 (2009).

Bourgault et al., "Reference-based pricing of prescription drugs: exploring the equivalence of angiotensin-converting-enzyme inhibitors," CMAJ, 161:255-60 (1999).

Brilla et al., Lisinopril-Mediated regression of myocardial fibrosis in patients with hypertensive heart disease. Circulation, 102:1388-1393 (2000).

Cabot Corporation, "Influence of CAB-O-SIL® M-5P on the Angle of Repose and Flow Rates of Pharmaceutical Powders," 10 pages (2004).

Calabro et al., "Hemodynamic effects of a single oral dose of enalapril among children with asymptomatic chronic mitral regurgitation," American Heart Journal, 138(5, Pt. 1), 955-961 (1999).

Definition of Hypertension (1 page) retrieved from: http://medical-dictionary.thefreedictionary.com/hypertension. No date available.

Delucchi et al., "Enalapril and prednisone in children with nephrotic-range proteinuria," Pediatric nephrology (Berlin, Germany) 14(12):1088-91 (2000).

Drug Information on Enalapril (3 pages), 2001. retrieved from: http://www.accessdata.fda.gov/drugsatfda_docs/nda/2001/18-998s058_Vasotec.cfm.

drugs.com. Enalapril Tablets Soluble. Website [online]. [available online May 9, 2010] [retrieved on Jan. 16, 2014], 11 pages. Retrieved from the Internet< URL: https://web.archive.org/web/20100509220009/http://www.drugs.com/pro/enalapril-tablets-soluble.html>. Enalapril Tablets Soluble—Clinical Pharmacology; Indications and Usage for Enalapril Tablets Soluble; Enalapril Tablets Soluble Dosage and Administration.

European Patent Application No. 13844343.7 Extended European Search Report dated Feb. 19, 2016.

Garrett, Edward R. Prediction of stability of drugs and pharmaceutical preparations. Journal of Pharmaceutical Sciences, 51(9):811-833 (1962).

Glass and Haywood, Stability considerations in liquid dosage forms extemporaneously prepared from commercially available products. J Pharmaceut Science, 9(3):398-426 (2006).

Glass et al. Stability considerations in liquid dosage forms extemporaneously prepared from commercially available products. Journal of Pharmacy & Pharmaceutical Sciences, 9(3):398-426 (2006).

Gulf Cooperation Council. The GCC Guidelines for Stability Testing of Drug Substances and Pharmaceutical Products. Publication [online]. Edition Two, 1428 H-2007 G [available online Jul. 2011] [retrieved on Feb. 3, 2014]. Retrieved from the Internet:< URL: https://web.archive.org/web/20110726040053/http://www.ich.org/fileadmin/Public_ Web_Site/ABOUT_ICH/Organisation/GCC/Topics under_Harmonisation/Stability.pdf>. p. 22, 2.9 .3; p. 25, 2.9.7.

Handbook of Pharmaceutical Excipients, Fifth edition, edited by Raymond C. Rowe et al., London: Pharmaceutical Press, 2006, (monographs for citric acid monohydrate, sodium benzoate, sodium citrate, sodium hydroxide, and xylitol), 23 pages.

Harris, Daniel C. Exploring Chemical Analysis, 4th edition. New York:W.H. Freeman and Company, 2009 (Chapters 8,9,21 and 22), 105 pages.

Hensel et al., Transesterification reactions off parabens (Alkyl 4-Hydroxybenzoates) with polyols in aqueous solution Journal of Pharmaceutical Sciences, 84(1):115-119 (1995).

Hsu et al., Enalapril in Infants With Single Ventricle: Results of a Multicenter Randomized Trial. Circulation, 122(4):333-340, (2010).

Hsu et al., "Rationale and design of a trial of angiotensin-converting enzyme inhibition in infants with single ventricle," American Heart Journal, 157(1):37-45 (2009).

Kalaitzidis et al. Prehypertension: is it relevant for nephrologists? Kidney International, 77:194-200 (2010).

Li et al., "Lessons learned from a pediatric clinical trial: The Pediatric Heart Network Angiotensin-Converting Enzyme Inhibition in Mitral Regurgitation Study," American Heart Journal, 161(2):233-240 (2011).

Liern et al., "The additive antiproteinuric effect of Enalapril and Losartan to normotensive patients with pathology proteinuria," Nefrologia : publicacion oficial de la Sociedad Espanola Nefrologia 24(6):553-8, (2004).

Lima et al., "Stability and in vitro release profile of enalapril maleate from different commercially available tablets: Possible therapeutic implications," Journ. Pharmac. and Biomed. Analysis, 47:934-937 (2008).

Lipshultz, "Exposure to anthracyclines during childhood causes cardiac injury," Seminars in Oncology, 33(3, Suppl. 8): S8-S14 (2006).

Ma et al., HPLC and LC-MS studies of the transesterification reaction of Methylparaben with twelve 3- to 6-carbon sugar alcohols and propylene glycol and the isomerization of the reaction products by acyl migration. Journal of Chromatograaphic Science, 40(3):170-177 (2002).

Meyers et al. Pharmacotherapy Review of Chronic Pediatric Hypertension. Clinical Therapeutics, 33(10):1331-1356 (2011).

Miller et al., "Enalapril: a well-tolerated and efficacious agent for the paediatric hypertensive patient," Journal of hypertension. Supplement : official journal of the International Society of Hypertension, 4(5):S413-6 (1986).

Miller et al., "Enalapril: a well-tolerated and efficacious agent for the pediatric hypertensive patient," Journal of cardiovascular pharmacology 10 Suppl 7S, 154-6 (1987).

Mir et al., "Effect of carvedilol on QT duration in pediatric patients with congestive heart failure," Clinical Drug Investigation, 24(1):9-15 (2004).

Momma, "ACE inhibitors in pediatric patients with heart failure," Paediatric drugs 8(1):55-69, (2006).

Nahata et al., Stability of Lisinopril in two liquid dosage forms. Ann Pharmacother. 38(3):396-9 (2004).

Nahata et al.Stability of enalapril maleate in three extemporaneously prepared oral liquids. Am. J. Health-Syst Pharm 55:1155-1157 (1998).

Nakamura et al., "The kinetic profiles of enalapril and enalaprilat and their possible developmental changes in pediatric patients with congestive heart failure," Clinical pharmacology and therapeutics. 56(2):160-8, (1994).

National institutes of Health. 'MedlinePius: Hypertension'. Website [online]. [available online May 20, 2012] [retrieved on Jan. 16, 2014], 5 pages. Retrieved from the Internet:< URL:https://web.archive.org/web/20120520035026/http://www.nlm.nih.gov/medlineplus/ency/article/000468.htm>.

(56) References Cited

OTHER PUBLICATIONS

Nationwide Children's Hospital. 'Enalapril Oral Suspension' Publication [online]. Mar. 29, 2010 [retrieved on Jan. 14, 2014], 1 page. etrieved from the Internet:< URL:http://www.nationwidechildrens.org/Document/Get/78785>.
Niazi, Sarfaraz K. Handbook of Pharmaceutical Manufacturing Formulations: Liquid Products, vol. 3, Second edition. New York: Information Healthcare USA, Inc., 2009, 400 pages.
Nicolosi et al., The prognostic value of predischarge quantitative two-dimensional echocardiographic measurements and the effects of early lisinopril treatment on left ventricular structure and function after acute myocardial infarction in the GISSI-3 trial. European Heart Journal, 17:1646-1656 (1996).
*Novartis AG* (Appellants) v. *Torrent Pharmaceuticals Limited, Apotex Inc., Mylan Pharmacuticals Inc.*, (Appellees), No. 2016-1352, Slip Opinion decided Apr. 12, 2017, 27 pages.
Nunn et al. Formulation of medicines for children. British Journal of Clinical Pharmacology, 59:6:674-676 (2005).
Packer et al., Comparative effects of low and high doses of the angiotensin-converting enzyme inhibitor, lisinopril, on morbidity and mortality in chronic heart failure. Circulation, 100:2312-1218 (1999).
Patel et al., "Extemporaneous Dosage Form for Oral Liquids," Pharmacophore, 2(2):86-103 (2011).
PCT Patent Application No. PCT/US2013/063096 International Preliminary Report on Patentability dated Apr. 7, 2015.
PCT Patent Application No. PCT/US2013/063096 International Search Report dated Feb. 20, 2014.
PCT Patent Application No. PCT/US2013/063096 Written Opinion dated Feb. 20, 2014.
PCT Patent Application No. PCT/US2017/023074 International Search Report and Written Opinion dated Jun. 16, 2017.
Product Information of Bicitra, "Sodium Citrate and Citric Acid Oral Solution USP." 2 pages.
Product Information of Ora-Sweet (1 page, 2013) retrieved from, http://www.stobec.com/documents/data/8196.pdf.
Proesmans et al., "Enalapril in children with Alport syndrome," Pediatric nephrology (Berlin, Germany) 19(3:271-5 (2004).
Proesmans et al., Long-term therapy with enalapril in patients with nephrotic-range proteinuriam, Pediatric nephrology (Berlin, Germany), 10(5):587-9 (1996).
Prosemans et al., "Enalapril in pediatric patients with Alport syndrome: 2 years' experience," European Journal of Pediatrics 159(6):430-433 (2000).
Raia, et al., Angiotensin-converting enzyme inhibitors: A Comparative review. DPIC, The Annuals of Pharmacotherapy, 24:506-525 (1990).
Ramusovic et al., "Determination of enalapril and enalaprilat in small human serum quantities for pediatric trials by HPLC-tandem mass spectrometry," Biomedical Chromatography 26(6):697-702 (2012).
Rezende et al., "Stability and Compatibility Study on Enalapril Maleate Using Thermoanalytical Techniques," Journal Thermal Analysis and Calorimetry, 93:3:881-886 (2008).
Rippley et al., "Pharmacokinetic Assessment of an Oral Enalapril Suspension for Use in Children," Biopharmaceutics & Drug Disposition 21:339-344 (2000).
Rokicki, "Use of converting enzyme inhibitors in children. I. General remarks," Wiadomosci lekarskie (Warsaw, Poland;: 1960) 50(1-3), 28-31 (1997).
Rose et al., Stability of Lisinopril syrup (2 mg/mL) extemporaneously compounded from tablets. Int J Pharm Compd. 4(5):398-399 (2000).
Russell, Craig Allen, Paediatric Drug Development:—Reformulation, In Vitro, Genomic and In Vivo Evaluation. Thesis, Apr. 2014, 330 pages.
Sandoz, Limited. Amoxicillin 125 mg/5 ml Powder for Oral Suspension. Product brochure [online]. Jul. 2012 [retrieved on Jan. 17, 2014]. 3 pages. Retrieved from the Internet< URL:http://www.drugs.com/uklpdf/leaflet/196044.pdf>.

Schlatter et al., Stability of Enalapril solutions prepared from tablets in sterile water. Australian J. Hospital Pharmacy, 27:395 (1997).
Seikaly. Hypertension in children: an update on treatment strategies. Current Opinion in Pediatrics, 19:170-177 (2007).
Silber et al., "Design and baseline characteristics for the ACE inhibitor alter anthracycline (AAA) study of cardiac dysfunction in long-term pediatric cancer survivors," American Heart Journal 142(4), 577-585 (2001).
Silber et al., "Enalapril to prevent cardiac function decline in long-term survivors of pediatric cancer exposed to anthracyclines," Journal of Clinical Oncology, 22(5):820-828 (2004).
*Silvergate Pharaceuticals, Inc.* (Plaintiff) v. *Bionpharma, Inc.* (Defendant) C.A. No. 1:16-cv-00876-SLR (consolidated). Bionpharma Inc.'s Invalidity Contentions Pursuant to Delaware Default Standard Rule 4(d). Jun. 9, 2017, 50 pages.
Simončič et al., "Use of microcalorimetry in determination of stability of enalapril maleate and enalapril maleate table formulations," Int'l. Journal Pharmaceutics, 342:145-151 (2007).
Sipahi et al. Effect of Antihypertensive Therapy on Incident Stroke in Cohorts with Prehypertensive Blood Pressure Levels: A Meta-Analysis of Randomized Controlled Trials, Stroke: Journal of the America! Heart Association [online], Dec. 8, 2011 (retrieved Jan. 16, 2014]. 10 pages. Retrieved from the Internet:< URL:http://www.medpagetoday.com/upload/2011/12/9/Stroke-2011-Sipahi-STROKEAHA.111.636829.pdf>.
Sipahi et al., Effects of normal, pre-hypertensive, and hypertensive blood pressure levels on progression of coronary atherosclerosis, J. Am. Coll. Cardiol. 48:833-838 (2006).
Sosnowska et al., "Stability of Extemporaneous Enalapril Maleate Suspensions for Pediatric Use Prepared from Commercially Available Tablets," Acta Poloniae Pharmaceutica, 66(3):321-326 (2009).
Standing et al. Paediatric formulations—Getting to the heart of the problem. International Journal of Pharmaceutics, 300(1-2):56-66 (2005).
Stanisz, "Evaluation of stability of enalapril maleate in solid phase," Journ. Pharma. and Biomed. Analysis, 31:375-380 (2003).
TEVA UK, Limited. Enalapril Maleate 2.5 mg, 5 mg, 10 mg and 20 mg Tablets. Product Brochure [online]. Mar. 2011 [retrieved on Jan. 14, 2014], 8 pages. Retrieved from the Internet:< URL:http://www.drugs.com/uk/pdf/leaflet/213793.pdf>. col. 2, lines 70-76.
Thompson et al., Characterization of an entemporaneous liquid formulation of lisinopril. Am J Health Syst Pharm. 60(1):69-74 (2003).
Tian et al., Effect of organic anion-transporting polypeptide 1B1 (OATP1B1) polymorphism on the single- and multiple-dose pharmacokinetics of enalapril in healthy Chinese adult men Clinical Therapeutics, 33(5):655 (2011).
U.S. Appl. No. 13/670,355 Office Action dated Feb. 8, 2013.
U.S. Appl. No. 13/670,355 Office Action dated Jul. 30, 2013.
U.S. Appl. No. 13/914,452 Office Action dated Aug. 28, 2013.
U.S. Appl. No. 14/433,502 Office Action dated Dec. 29, 2016.
U.S. Appl. No. 15/081,603 First Action Interview dated Sep. 2, 2016.
U.S. Appl. No. 15/081,603 First Action Interview Office Action Summary dated Jan. 17, 2017.
U.S. Appl. No. 15/433,743 Office Action dated Jun. 5, 2017.
U.S. Appl. No. 15/613,622 Office Action dated Aug. 11, 2017.
Van Hecken et al. Absence of a pharmacokinetic interaction between enalapril and frusemide British Journal of Clinical Pharmacology, 23:84-87 (1987).
Vasotec (Enalapril Maleate) Product Insert, 5 pages (2010) (Best copy available).
Wang et al., "Eudragit E Accelerated the Diketopiperazine Formation of Enalapril Maleate Determined by Thermal FTIR Microspectroscopic Technique," Pharmaceutical Research, vol. 21, No. 11, Nov. 2004.
Webster et al., The Stability of Lisinopril as an extemporaneous syrup. Int J Pharm Compd. 1(5):352-353 (1997).
Wells et al., "A double-blind, placebo-controlled, dose-response study of the effectiveness and safety of enalapril for children with hypertension," Journal of Clinical Pharmacology 42(8), 870-880 (2002).

(56) References Cited

OTHER PUBLICATIONS

Wells et al., "The Pharmacokinetics of Enalapril in Children and Infants with Hypertension," J. Clin Pharmacol 41:1064-1074 (2001).
Williams et al, "Factors affecting growth in infants with single ventricle physiology: a report from the Pediatric Heart Network Infant Single Ventricle Trial," The Journal of Pediatrics, 159(6), 1017-22.e2 (2011).

ENALAPRIL COMPOSITIONS

CROSS REFERENCE

This application is a continuation of U.S. patent application Ser. No. 15/433,743, filed Feb. 15, 2017, which is a continuation of U.S. patent application Ser. No. 14/433,502, filed Apr. 3, 2015; which is a U.S. National Stage of PCT/US2013/063096, filed Oct. 2, 2013; which is a continuation of U.S. patent application Ser. No. 13/914,452, filed Jun. 10, 2013, now U.S. Pat. No. 8,778,366, issued Jul. 15, 2014; which is a continuation of U.S. patent application Ser. No. 13/670,355, filed on Nov. 6, 2012, now U.S. Pat. No. 8,568,747, issued Oct. 29, 2013; which claims the benefit of U.S. Patent Application No. 61/710,489, filed Oct. 5, 2012, all of which are incorporated herein by reference in their entirety.

BACKGROUND OF THE INVENTION

Hypertension, or high blood pressure, is a serious health issue in many countries. According to the National Heart Blood and Lung Institute, it is thought that about 1 in 3 adults in the United States alone have hypertension. Left unchecked, hypertension is considered a substantial risk factor for cardiovascular and other diseases including coronary heart disease, myocardial infarction, congestive heart failure, stroke and kidney failure. Hypertension is classified as primary (essential) hypertension or secondary hypertension. Primary hypertension has no known cause and may be related to a number of environmental, lifestyle and genetic factors such as stress, obesity, smoking, inactivity and sodium intake. Secondary hypertension can be caused by drug or surgical interventions, or by abnormalities in the renal, cardiovascular or endocrine system.

A number of antihypertensive drugs are available for treating hypertension. Various therapeutic classes of antihypertensive drugs include alpha-adrenergic blockers, beta-adrenergic blockers, calcium-channel blockers, hypotensives, mineralcorticoid antagonists, central alpha-agonists, diuretics and renin-angiotensin-aldosterone inhibitors which include angiotensin II receptor antagonists (ARB) and angiotensin-converting enzyme (ACE) inhibitors. Angiotensin-converting enzyme (ACE) inhibitors inhibit angiotensin-converting enzyme (ACE), a peptydyl dipeptidase that catalyzes angiotension I to angiotension II, a potent vasoconstrictor involved in regulating blood pressure.

Enalapril is a prodrug belonging to the angiotensin-converting enzyme (ACE) inhibitor of medications. It is rapidly hydrolyzed in the liver to enalaprilat following oral administration. Enalaprilat acts as a potent inhibitor of ACE. The structural formulae of enalapril and enalaprilat is as follows:

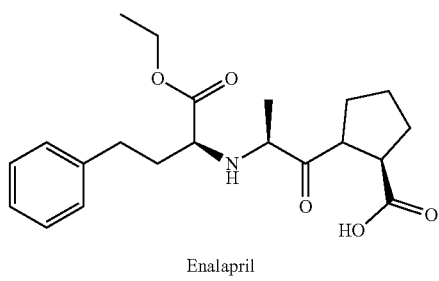

Enalapril

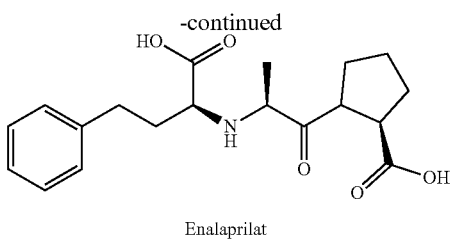

Enalaprilat

Enalapril is currently administered in the form of oral tablets, (e.g., Vasotec®). In addition to the treatment of hypertension, enalapril tablets have been used for symptomatic congestive heart failure, and asymptomatic left ventricular dysfunction.

SUMMARY OF THE INVENTION

Provided herein are enalapril powder compositions for an oral liquid formulation. In one aspect, the powder comprises (a) about 1 to about 30% (w/w) enalapril or a pharmaceutically acceptable salt thereof, and (b) about 60 to about 99% (w/w) mannitol. In some embodiments, when the powder is reconstituted into an oral liquid, the liquid is homogenous and stable for at least 12 weeks at ambient or refrigerated conditions. In other embodiments, the powder is stable for at least six months at ambient, accelerated or refrigerated conditions. In certain instances, ambient conditions are 25±5° C. and 55±10% relative humidity. In certain instances, refrigerated conditions are 5±3° C. In certain instances, accelerated conditions are about 40° C. or 60° C. and/or up to 80% relative humidity.

In another aspect, the powder comprises (a) about 1 to about 30% (w/w) enalapril or a pharmaceutically acceptable salt thereof, (b) about 60 to about 99% (w/w) mannitol, and (c) about 0.5 to about 2% (w/w) colloidal silicon dioxide. In some embodiments, when the powder is reconstituted into an oral liquid, the liquid is homogenous and stable for at least 12 weeks at ambient or refrigerated conditions. In other embodiments, the powder is stable for at least six months at ambient, accelerated or refrigerated conditions.

In certain embodiments, the enalapril is enalapril maleate. In certain embodiments, the powder is reconstituted in water for the oral liquid. In certain embodiments, the powder is reconstituted in a syrup for the oral liquid. In certain embodiments, the powder further comprises a pharmaceutically acceptable excipient. In certain instances, the pharmaceutically acceptable excipient is a sweetener, flavoring agent or preservative. In certain instances, the pharmaceutically acceptable excipient is a sweetener. In certain instances, the sweetener is a solid. In certain instances, the powder further comprises a solid (e.g., powder) sweetener. In certain instances, the sweetener is a liquid. In certain instances, the powder is reconstituted in a liquid sweetener (e.g., syrup). In certain embodiments, the enalapril or pharmaceutically acceptable salt thereof is about 12 to about 15% (w/w). In certain embodiments, the mannitol is about 80 to 85% (w/w). In certain embodiments, the silicon dioxide is about 1% (w/w). In certain embodiments, the enalapril or pharmaceutically acceptable salt thereof is about 14% (w/w), the mannitol is about 85% (w/w) and the silicon dioxide is about 1% (w/w). In certain embodiments, the powder comprises about 150 mg enalapril, about 890 mg mannitol and 10 mg colloidal silicon dioxide.

In another aspect, the powder comprises (a) about 1 to about 30% (w/w) enalapril or a pharmaceutically acceptable salt thereof, (b) about 60 to about 99% (w/w) mannitol, and (c) about 0.5 to about 2% (w/w) colloidal silicon dioxide, wherein, when the powder is reconstituted into an oral liquid, the liquid maintains no more than 5% total impurities for at least 12 weeks at ambient or refrigerated conditions. In another aspect, the powder comprises (a) about 1 to about 30% (w/w) enalapril or a pharmaceutically acceptable salt thereof, (b) about 60 to about 99% (w/w) mannitol, and (c) about 0.5 to about 2% (w/w) colloidal silicon dioxide, wherein, the powder maintains no more than 5% total impurities for at least six months at ambient, accelerated or refrigerated conditions.

In certain embodiments, the liquid maintains no more than 2.5% total impurities for at least 12 weeks. In certain embodiments, the liquid maintains no more than 2.5% enalaprilat for at least 12 weeks. In certain embodiments, the liquid maintains no more than 2.5% diketopiperazine for at least 12 weeks. In certain embodiments, the powder maintains no more than 2.5% total impurities for at least six months. In certain embodiments, the powder maintains no more than 1% enalaprilat for at least six months. In certain embodiments, the powder maintains no more than 1% diketopiperazine for at least six months.

Also provided herein are enalapril oral liquid formulations. In one aspect, the liquid formulation comprises (a) about 0.5 to about 5 mg/mL enalapril or a pharmaceutically acceptable salt thereof, (b) about 3 to about 10 mg/mL mannitol, and (c) a sweetener; wherein, the liquid is homogenous and stable for at least 12 weeks at ambient or refrigerated conditions.

In another aspect, the liquid formulation comprises (a) about 0.5 to about 5 mg/mL enalapril or a pharmaceutically acceptable salt thereof, (b) about 3 to about 10 mg/mL mannitol, (c) about 0.03 to about 0.13 mg/mL colloidal silicon dioxide, and (d) a sweetener; wherein, the liquid is homogenous and stable for at least 12 weeks at ambient or refrigerated conditions.

In certain embodiments, the enalapril is enalapril maleate. In certain embodiments, the liquid formulation comprises about 1 mg/mL enalapril. In certain embodiments, the liquid formulation comprises about 5 mg/mL mannitol. In certain embodiments, the liquid formulation comprises about 6 mg/mL mannitol. In certain embodiments, the liquid formulation comprises about 0.06 mg/mL colloidal silicon dioxide. In certain embodiments, liquid formulation comprises about 1 mg/mL enalapril, about 6 mg/mL mannitol and about 0.06 mg/mL colloidal silicon dioxide.

In certain embodiments, the sweetener is sorbitol. In certain embodiments, the liquid formulation comprises an additional pharmaceutically acceptable excipient. In certain instances, the pharmaceutically acceptable excipient is a flavoring agent or preservative. In certain embodiments, the liquid formulation comprises water as the liquid vehicle. In certain embodiments, the liquid formulation comprises a syrup as the liquid vehicle.

In another aspect, the liquid formulation comprises (a) about 1 mg/ml enalapril or a pharmaceutically acceptable salt thereof, (b) about 6 mg/ml mannitol, (c) about 0.07 mg/ml colloidal silicon dioxide, and (d) a sweetener, wherein the liquid formulation maintains an 80-125% $C_{max}$ of 58 ng/mL following oral administration at a 10 mg enalapril dosage for at least 12 weeks.

In some embodiments, when the liquid formulation is stored at up to 12 weeks at ambient or refrigerated conditions after reconstitution, the liquid formulation provides an 80-125% $C_{max}$ of 58 ng/mL enalapril following oral administration at a 10 mg enalapril dosage. In some embodiments, when the liquid formulation is stored at up to 12 weeks at ambient or refrigerated conditions, the liquid formulation provides an 80-125% $C_{max}$ of 41 ng/mL enalaprilat following oral administration at a 10 mg enalapril dosage.

In some embodiments, when the liquid formulation is stored at up to 12 weeks at ambient or refrigerated conditions after reconstitution, the liquid formulation provides an 80-125% $AUC_{inf}$ of 102.6 h*ng/mL enalapril following oral administration at a 10 mg enalapril dosage. In some embodiments, when the liquid formulation is stored at up to 12 weeks at ambient or refrigerated conditions, the liquid formulation provides an 80-125% $AUC_{inf}$ of 405.3 h*ng/mL enalaprilat following oral administration at a 10 mg enalapril dosage.

In some embodiments, when the liquid formulation is stored at up to 12 weeks at ambient or refrigerated conditions after reconstitution, the liquid formulation provides an 80-125% $T_{max}$ of 0.87 h for enalapril following oral administration at a 10 mg enalapril dosage. In some embodiments, when the liquid formulation is stored at up to 12 weeks at ambient or refrigerated conditions, the liquid formulation provides an 80-125% $T_{max}$ of 3.45 h for enalaprilat following oral administration at a 10 mg enalapril dosage.

Also provided herein are processes for preparing an enalapril oral liquid formulation. In one aspect, the process comprises the steps of (i) providing an uniform powder comprising about 10 to about 20% (w/w) enalapril or a pharmaceutically acceptable salt thereof, about 60 to about 90% (w/w) mannitol, and about 0.5 to about 1% (w/w) colloidal silicon dioxide in a bottle; (ii) adding an amount of sweetener in liquid syrup form; (iii) shaking the liquid formulation for at least 10 seconds; (iv) adding a second amount of sweetener in liquid syrup form; (v) shaking the liquid formulation for at least 10 seconds; and (vi) allowing the formulation in the bottle to stand for at least one hour to allow bubble dissipation.

Also provided herein are methods of treating hypertension or heart failure comprising administering to a patient in need thereof an oral liquid formulation reconstituted from an enalapril powder as described herein. In one embodiment, the patient is a child. In another embodiment, the patient is elderly.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Reconstitution of various enalapril powder compositions.

DETAILED DESCRIPTION OF THE INVENTION

Figure 1:
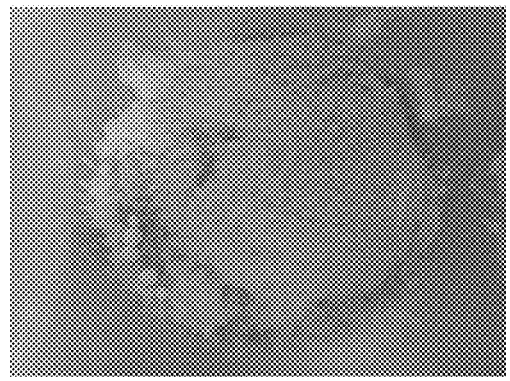
FIG. 1: Scaled-up enalapril powder composition A blended for 60 minutes showing formulation of balls and segregation.

Provided herein are stable enalapril powder compositions for oral liquid administration. Also provided herein are stable enalapril oral liquid compositions. These enalapril compositions described herein are useful for the treatment of hypertension, heart failure as well as ventricular dysfunction. The compositions are advantageous over conventional solid dosage administration of enalapril ranging from ease of administration, better absorption, accessibility to additional patient populations such as to children and the elderly, and an increased patient compliance to medication.

It is generally known that certain segments of the population have difficulty ingesting and swallowing solid oral dosage forms such as tablets and capsules. As many as a quarter of the total population has this difficulty. Often, this leads to non-compliance with the recommended medical therapy with the solid dosage forms, thereby resulting in rending the therapy ineffective. Further, solid dosage forms are not recommended for children or elderly due to increased risk in choking.

For enalapril, the current solution to overcoming the use of the tablet form is for a compounding pharmacist to pulverize and crush the enalapril tablet(s) into a powder via mortar and pestle and reconstitute the powder in some liquid form. However forming a enalapril oral liquid in this fashion has significant drawbacks including large variability in the actual dosage, incomplete solubilizing of the enalapril tablet in the liquid, rapid instability, inconsistent formulation methods per compounding pharmacy, and a number other potential issues. The crushed tablet liquid formulation may also be potentially unsafe due to contamination with residual drugs and other substances from the mortar and pestle or other crushing agent.

The present embodiments provide a safe and effective oral administration of enalapril for the treatment of hypertension and other disorders. In particular, the embodiments provide stable enalapril oral liquid compositions as well as enalapril powder compositions for oral liquid administration.

As used herein, "enalapril" refers to enalapril base, its salt, or solvate or derivative or isomer or polymorph thereof. Suitable compounds include the free base, the organic and inorganic salts, isomers, isomer salts, solvates, polymorphs, complexes etc. U.S. Pat. Nos. 4,374,829; 4,472,380 and 4,510,083 disclose exemplary methods in the preparation of enalapril. In some embodiments, the enalapril used in the compositions described herein is an enalapril salt. In some instances, the enalapril salt is enalapril maleate. In other instances, the enalapril salt is in the form of enalapril sodium.

Other ACE inhibitors are contemplated in the formulations within and include but are not limited to quinapril, indolapril, ramipril, perindopril, lisinopril, benazepril, imidapril, zofenopril, trandolapril, fosinopril, captopril, and their salts, solvates, derivatives, polymorphs, complexes, thereof.

Enalapril Powder Compositions

In one aspect, enalapril powder compositions herein comprise enalapril and mannitol as a stabilizing agent. By itself, enalapril is temperature stable under dry or stable conditions. However, when mixed in a matrix such as in a tablet with additional excipients, enalapril is unstable and can degrade to an unwanted cyclized diketopiperazine (DKP).

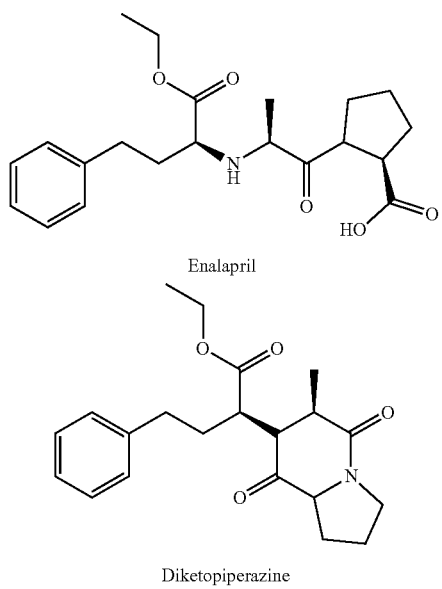

Enalapril

Diketopiperazine

It is contemplated that lactose in enalapril solid tablet formulations aid in preventing degradation to diketopiperazine and/or other related substances. However, surprisingly, as shown in Example 1, powder blends of lactose with enalapril showed the greatest degradation whereas enalapril/mannitol powder was most stable under accelerated conditions. This was also observed for the prepared solutions from the powder blends (Example 2).

In some embodiments, enalapril is present in about 1% w/w to about 30% w/w of the powder composition. In some embodiments, enalapril is present in about 2% w/w to about 25% w/w, about 5% w/w to about 20% w/w, about 7% w/w to about 18% w/w, about 10% w/w to about 16% w/w, or about 12% w/w to about 15% w/w of the powder composition. In other embodiments, enalapril is present in about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w or about 30% w/w of the powder composition. In certain embodiments, enalapril is present in about 1% w/w of the powder composition. In certain other embodiments, enalapril is present in about 2% w/w of the powder composition. In certain other embodiments, enalapril is present in about 10% w/w of the powder composition. In certain other embodiments, enalapril is present in about 14% w/w of the powder composition. In certain other embodiments, enalapril is present in about 15% w/w of the powder composition. In certain other embodiments, enalapril is present in about 20% w/w of the powder composition.

In some embodiments, mannitol is present in about 60% w/w to about 99% w/w of the powder composition. In some embodiments, mannitol is present in about 65% w/w to about 95% w/w, about 70% w/w to about 90% w/w or about 75% w/w to about 85% w/w of the powder composition. In other embodiments, mannitol is present in about 99% w/w, about 98% w/w, about 97% w/w, about 96% w/w, about 95% w/w, about 94% w/w, about 93% w/w, about 92% w/w, about 91% w/w, about 90% w/w, about 89% w/w, about 88% w/w, about 87% w/w, about 86% w/w, about 85% w/w, about 84% w/w, about 83% w/w, about 82% w/w, about 81% w/w, about 80% w/w, about 79% w/w, about 78% w/w, about 77% w/w, about 76% w/w, about 75% w/w, about 74% w/w, about 73% w/w, about 72% w/w, about 71% w/w, about 70% w/w, about 69% w/w, about 68% w/w, about 67% w/w, about 66% w/w, about 65% w/w, about 64% w/w, about 63% w/w, about 62% w/w, about 61% w/w or about 60% w/w of the powder composition. In certain embodiments, mannitol is present in about 1% w/w of the powder composition. In certain other embodiments, mannitol is present in about 99% w/w of the powder composition. In certain other embodiments, mannitol is present in about 90% w/w of the powder composition. In certain other embodiments, mannitol is present in about 85% w/w of the powder composition. In certain other embodiments, mannitol is present in about 80% w/w of the powder composition. In certain other embodiments, mannitol is present in about 70% w/w of the powder composition. In certain other embodiments, mannitol is present in about 60% w/w of the powder composition.

In further embodiments, the enalapril powder compositions herein comprises additional excipients including, but not limited, to buffering agents, glidants, preservatives, sweeteners, flavoring agents, coloring agents and thickeners. Additional excipients such as bulking agents, tonicity agents and chelating agents are within the scope of the embodiments.

Buffering agents maintain the pH when enalapril powder compositions are reconstituted into a liquid form. Non-limiting examples of buffering agents include, but are not limited to, sodium bicarbonate, potassium bicarbonate, magnesium hydroxide, magnesium lactate, magnesium glucomate, aluminum hydroxide, aluminum hydroxide/sodium bicarbonate co precipitate, a mixture of an amino acid and a buffer, a mixture of aluminum glycinate and a buffer, a mixture of an acid salt of an amino acid and a buffer, and a mixture of an alkali salt of an amino acid and a buffer. Additional buffering agents include sodium citrate, sodium tartarate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts. Some buffering agents also impart effervescent qualities when a powder is reconstituted in a solution. In some embodiments, the enalapril powder compositions described herein comprise a buffering agent.

Glidants are substances that improve flowability of a powder. Suitable glidants include, but are not limited to, calcium phosphate tribasic, calcium silicate, cellulose (powdered), colloidal silicon dioxide, magnesium silicate, magnesium trisilicate, silicon dioxide, starch, talc and the like. In some embodiments, the enalapril powder compositions described herein comprise a glidant. In certain instances, enalapril powder compositions described herein comprise colloidal silicon dioxide.

Preservatives include anti-microbials, anti-oxidants, and agents that enhance sterility. Exemplary preservatives include ascorbic acid, ascorbyl palmitate, BHA, BHT, citric acid, erythorbic acid, fumaric acid, malic acid, propyl gallate, sodium ascorbate, sodium bisulfate, sodium metabisulfite, sodium sulfite, parabens (methyl-, ethyl-, butyl-), benzoic acid, potassium sorbate, vanillin, and the like. In some embodiments, the enalapril powder compositions described herein comprise a preservative.

Sweeteners or sweetening agents include any compounds that provide a sweet taste. This includes natural and synthetic sugars, natural and artificial sweeteners, natural extracts and any material that initiates a sweet sensation in a subject. In some embodiments, the enalapril powder compositions described herein comprise a sweetener. Solid, powder sweeteners, in some embodiments, are blended with the enalapril powder compositions described herein. In other embodiments, sweeteners in liquid form referred to as syrups are used to solvate or dissolve the enalapril powder compositions described herein.

Sugars illustratively include glucose, fructose, sucrose, xylitol, tagatose, sucralose, maltitol, isomaltulose, Isomalt™ (hydrogenated isomaltulose), lactitol, sorbitol, mannitol, erythritol, trehalose, maltodextrin, polydextrose, and the like. Other sweeteners illustratively include glycerin, inulin, erythritol, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrolysates, maltitol syrup, high fructose corn syrup, etc., and as branded products, e.g., Sweet Am™ liquid (Product Code 918.003—propylene glycol, ethyl alcohol, and proprietary artificial flavor combination, Flavors of North America) and Sweet Am™ powder (Product Code 918.005—maltodextrin, sorbitol, and fructose combination and Product Code 918.010—water, propylene glycol, sorbitol, fructose, and proprietary natural and artificial flavor combination, Flavors of North America), Pro-Sweet™ (1-10% proprietary plant/vegetable extract and 90-99% dextrose combination, Virginia Dare), Maltisweet™ (maltitol solution, Ingredion) and Sorbo™ (sorbitol and sorbitol/xylitol solution, SPI Polyols), Invertose™ (high fructose corn syrup, Ingredion) and Ora-Sweet® sugar-free flavored syrup (Paddock Laboratories, Inc.). Sweeteners can be used singly or in combinations of two or more. Suitable concentrations of different sweeteners can be selected based on published information, manufacturers' data sheets and by routine testing. In certain instances, an above-described syrup is used to solvate or dissolve the enalapril powder compositions described herein. In further instances, Ora-Sweet® sugar-free flavored syrup is used to solvate or dissolve the enalapril powder compositions described herein.

In some embodiments, the sweetener imparts a sweet sensation equivalent to an about 50 to about 95% w/v sucrose in water. In some embodiments, the sweetener imparts a sweet sensation equivalent to an about 50% w/v, about 55% w/v, about 60% w/v, about 65% w/v, about 70% w/v, about 75% w/v, about 85% w/v (e.g., simple syrup NF), about 90% w/v, or about 95% w/v sucrose in water. In some embodiments, the sweetener imparts a sweet sensation equivalent to an about 60% to about 80% w/v sorbitol in water. In some embodiments, the sweetener imparts a sweet sensation equivalent to an about 60% w/v, about 65% w/v, about 70% w/v, about 75% w/v or about 80% w/v sorbitol in water. In some embodiments, the sweetener imparts a sweet sensation equivalent to an about 64% w/v sorbitol in water.

In another embodiment, the enalapril powder compositions comprise a flavoring agent or flavorant to enhance the taste or aroma of the composition in liquid form. Suitable natural or synthetic flavoring agents can be selected from standard reference books, for example Fenaroli's Handbook of Flavor Ingredients, 3rd edition (1995). Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, vanilla, wintergreen, etc. Also useful, particularly where the composition is intended primarily for pediatric use, is tutti-frutti or bubble-gum flavor, a compounded flavoring agent based on fruit flavors. Presently preferred flavoring agents include anise, cinnamon, cacao, orange, peppermint, cherry (in particular wild cherry), grape, bubblegum and vanilla. In some embodiments, the enalapril powder compositions described herein comprise a wild cherry flavoring agent. Flavoring agents can be used singly or in combinations of two or more.

In further embodiments, the enalapril powder compositions comprise a coloring agent for identity and/or aesthetic purposes of the resultant liquid form. Suitable coloring agents illustratively include FD&C Red No. 3, FD&C Red No. 20, FD&C Red No. 40, FD&C Yellow No. 6, FD&C Blue No. 2, D&C Green No. 5, D&C Orange No. 5, caramel, ferric oxide and mixtures thereof.

Thickeners impart viscosity or weight to the resultant liquid forms from the enalapril compositions described herein. Exemplary thickeners include dextrin, cellulose derivatives (ethylcellulose, hydroxyethyl cellulose, methylcellulose, hypromellose, and the like) starches, pectin, polyethylene glycol, polyethylene oxide, trehalose and certain gums (xanthan gum, locust bean gum, etc.). In certain embodiments, the enalapril powder compositions comprise a thickener.

Additional excipients are contemplated in the enalapril powder composition embodiments. These additional excipients are selected based on function and compatibility with the enalapril powder compositions described herein and may be found, for example in *Remington: The Science and Practice of Pharmacy*, Nineteenth Ed (Easton, Pa.: Mack Publishing Company, 1995); Hoover, John E., *Remington's Pharmaceutical Sciences*, (Easton, Pa.: Mack Publishing Co 1975); Liberman, H. A. and Lachman, L., Eds., *Pharmaceutical Dosage Forms* (New York, N.Y.: Marcel Decker 1980); and *Pharmaceutical Dosage Forms and Drug Delivery Systems*, Seventh Ed (Lippincott Williams & Wilkins 1999), herein incorporated by reference in their entirety.

In certain embodiments, an additional excipient is present in about 1% w/w to about 30% w/w of the enalapril powder composition. In certain embodiments, an additional excipient is present in about 2% w/w to about 25% w/w, about 5% w/w to about 20% w/w, about 7% w/w to about 15 w/w or about 10% w/w to about 12% w/w of the enalapril powder composition. In other embodiments, an additional excipient is present in about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w or about 30% w/w of the enalapril powder composition.

Preparation of Enalapril Powder Compositions

Preparation of enalapril powder compositions described herein includes any known pharmaceutical method. In one embodiment, the enalapril powder compositions described herein are prepared by a granulation method. In an exemplary granulation method, enalapril is dissolved in water or a solution (e.g., sodium bicarbonate) which is subsequently sprayed onto mannitol. The wetted material is then dried via heat (e.g., 40°-60° C. oven) or air-dried. The dried granulation is then passed through a 40-mesh screen, for example.

In another embodiment, the enalapril powder compositions described herein are prepared by a direct blend method. In one example, enalapril is blended with mannitol along with any other excipients in a dry mixer or blender. In certain instances, the powders are passed through a mesh screen prior to and/or after mixing. The dry blend is facilitated by conventional large-scale mixing equipment such as rotating-shell mixers (e.g., drum-type, cubical shaped, double-cone and twin-shell blender), fixed-shell (ribbon) mixers, sigma-blade and planetary paddle mixers, vertical impeller mixers and motionless mixers. The mixing is performed to blend uniformity of the enalapril powder compositions described herein. In embodiments with additional excipients, mixing methods can include all components together or incorporate certain components together first with other components subsequently added.

In an additional embodiment, the enalapril powder compositions described herein additionally comprise colloidal silicon dioxide in scale-up preparation. Although colloidal silicon dioxide has been reported to decrease stability of enalapril, (Rezende et al., Stability and Compatibility Study on Enalapril Maleate using Thermoanalytical Techniques, *J. Thermal Anal. & calorimetry*, 2008 (93) 881-886), the addition of colloidal silicon dioxide surprisingly aided in the uniformity of the blend and the bottle content as well as in preparation of the liquid form (see Example 4).

In some embodiments, colloidal silicon dioxide is present in about 0.1% w/w to about 2% w/w of the powder composition. In some embodiments, colloidal silicon dioxide is present in about 0.1% w/w to about 2% w/w, about 0.2% w/w to about 1.7% w/w, about 0.3% w/w to about 1.5%, about 0.4% w/w to about 1.2% or about 0.5% w/w to about 1.0% w/w of the powder composition. In other embodiments, colloidal silicon dioxide is present in about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w or about 2.0% w/w of the powder composition. In certain embodiments, colloidal silicon dioxide is present in about 0.1% w/w of the powder composition. In certain other embodiments, colloidal silicon dioxide is present in about 0.5% w/w of the powder composition. In certain other embodiments, colloidal silicon dioxide is present in about 1.0% w/w of the powder composition. In certain other embodiments, colloidal silicon dioxide is present in about 1.2% w/w of the powder composition. In certain other embodiments, colloidal silicon dioxide is present in about 1.5% w/w of the powder composition. In certain other embodiments, colloidal silicon dioxide is present in about 1.7% w/w of the powder composition. In certain other embodiments, colloidal silicon dioxide is present in about 2.0% w/w of the powder composition.

Stability of Enalapril Powder Compositions

The enalapril powder compositions described herein are stable in various storage conditions including refrigerated, ambient and accelerated conditions. Stable as used herein refer to enalapril powder compositions having about 95% enalapril and about 5% or less total impurities or substances at the end of a given storage period. Stability is assessed by HPLC or any other known testing method. In some embodiments, the stable enalapril powder compositions have about 5%, about 4%, about 3%, about 2.5%, about 2%, about 1.5%, about 1%, or about 0.5% total impurities or substances. In other embodiments, the stable enalapril powder compositions have about 5% total impurities or substances. In yet other embodiments, the stable enalapril powder compositions have about 4% total impurities or substances. In yet other embodiments, the stable enalapril powder compositions have about 3% total impurities or substances. In yet other embodiments, the stable enalapril powder compositions have about 2% total impurities or substances. In yet other embodiments, the stable enalapril powder compositions have about 1% total impurities or substances. In further embodiments, the stable enalapril powder compositions have about 95%, about 96%, about 97%, about 98% or about 99% enalapril at the end of a given storage period.

At refrigerated and ambient conditions, the enalapril powder compositions described herein are stable for at least 1 month, at least 2 months, at least 3 months, at least 6 months, at least 9 months, at least 12 months, at least 15 months, at least 18 months, at least 24 months, at least 30 months and at least 36 months. At accelerated conditions, the enalapril powder compositions described herein are stable for at least 1 month, at least 2 months, at least 3 months, at least 4 months, at least 5 months, at least 6 months, at least 7 months, at least 8 months, at least 9 months, at least 10 months, at least 11 months or at least 12 months. Accelerated conditions include temperature and/or relative humidity (RH) that are above ambient levels (e.g. 25±5° C.; 55±10% RH). In some instances, an accelerated condition is at about 30° C., about 35° C., about 40° C., about 45° C., about 50° C., about 55° C. or about 60° C. In other instances, an accelerated condition is above 65% RH, about 70% RH, about 75% RH or about 80% RH. In further instances, an accelerated condition is about 40° C. or 60° C. at ambient humidity. In yet further instances, an accelerated condition is about 40° C. at 75±5% RH humidity. Ambient conditions include temperature and/or relative humidity (RH) that are at ambient levels (e.g. 25±5° C.; 55±10% RH). In some instances, an ambient condition is at about 20° C., about 21° C., about 22° C., about 23° C., about 24° C., about 25° C., about 26° C., about 27° C., about 28° C., about 29° C., or about 30° C. In other instances, an ambient condition is about 45% RH, about 50% RH, about 55% RH, about 60% RH or about 65% RH. Refrigerated conditions include temperature and/or relative humidity (RH) in typical refrigeration units (e.g., 5±3° C.). In some instances, a refrigerated condition is at about 2° C., about 3° C., about 4° C., about 5° C., about 6° C., about 7° C. or about 8° C. In other instances, a a refrigerated condition is at about 4° C.

Enalapril Oral Liquid Compositions

In another aspect, enalapril powder compositions described herein are useful for the preparation or reconstitution of an enalapril oral liquid. Oral liquids include, but are not limited to, solutions (both aqueous and nonaqueous), suspensions, emulsions, syrups, slurries, juices, elixirs, dispersions, and the like. It is envisioned that solution/suspensions are also included where certain components of the enalapril powder compositions described herein are in a solution while other components are in a suspension. By way of illustrative example only, when an enalapril powder composition comprising enalapril, mannitol and an excipient such as colloidal silicon dioxide or a powdered cellulose is dissolved in water or other aqueous solvent, the enalapril and mannitol are in solution whereas the colloidal silicon dioxide or powdered cellulose would form a suspension in the aqueous environment. In some embodiments, the enalapril oral liquid compositions are solutions. In other embodiments, the enalapril oral liquid compositions are suspensions. In yet other embodiments, the enalapril oral liquid compositions are solution/suspensions.

Liquid vehicles suitable for the enalapril powder compositions described herein are selected for a particular oral liquid composition (solution, suspension, etc.) as well as other qualities such as clarity, toxicity, viscosity, compatibility with excipients, chemical inertness, palatability, odor, color and economy. Exemplary liquid vehicles include water, ethyl alcohol, glycerin, propylene glycol, syrup (sugar or other sweetener based, e.g., Ora-Sweet® SF sugar-free flavored syrup), juices (apple, grape, orange, cranberry, cherry, tomato and the like), other beverages (tea, coffee, soft drinks, milk and the like), oils (olive, soybean, corn, mineral, castor and the like), and combinations or mixtures thereof. Certain liquid vehicles, e.g., oil and water, can be combined together to form emulsions. In some embodiments, water is used for as a vehicle for an enalapril oral liquid. In other embodiments, a syrup is used for as a vehicle for an enalapril oral liquid. In yet other embodiments, a juice is used for as a vehicle for an enalapril oral liquid.

The enalapril liquids prepared from the powder compositions described herein, in some embodiments, are homogenous. Homogenous liquids as used herein refer to those liquids that are uniform in appearance, identity, consistency and drug concentration per volume. Non-homogenous liquids include such liquids that have varied coloring, viscosity and/or aggregation of solid particulates, as well as non-uniform drug concentration in a given unit volume. Homogeneity in liquids are assessed by qualitative identification or appearance tests and/or quantitative HPLC testing or the like. Such exemplary tests include visual inspection of the resultant liquid for air bubbles and/or undissolved solids which may cause variable dosing. Analytical HPLC testing can also determine drug concentration uniformity by examining aliquots of certain volume sections (e.g., 5 or 10 mL from the top, middle and bottom of a 150 mL bottle). The mixing methods and excipients described herein are selected to impart a homogenous quality to a resultant enalapril liquid.

Mixing methods encompass any type of mixing that results in a homogenous enalapril liquid composition. In some embodiments, a quantity of an enalapril powder composition is added to a liquid vehicle and then mixed by a stirring, shaking, swirling, agitation element or a combination thereof. In certain instances, a fraction of an enalapril powder composition (i.e., one-half, one-third, one-fourth, etc.) is added to a liquid vehicle, mixed by stirring, shaking, swirling, agitation or a combination thereof, and the subsequent powder fraction(s) is added and mixed. In other embodiments, a liquid vehicle is added to an enalapril powder composition in a container, for example, a bottle, vial, bag, beaker, syringe, or the like. The container is then mixed by stirring, shaking, swirling, agitation, inversion or a combination thereof. In certain instances, a fractional volume of the liquid vehicle (i.e., one-half, one-third, one-fourth volume, etc.) is added to an enalapril powder composition in a container, mixed by stirring, shaking, swirling, agitation, inversion or a combination thereof; and the subsequent liquid fraction(s) is added and mixed. In certain instances, a one-half fractional volume of the liquid vehicle is added to an enalapril powder composition in a container and mixing by shaking; the other one-half fractional volume of the liquid vehicle is then subsequently added and mixed. In any of the above embodiments, mixing (i.e., stirring, shaking, swirling, agitation, inversion or a combination thereof) occurs for a certain time intervals such as about 10 seconds, about 20 seconds, about 30 seconds, about 45 seconds, about 60 seconds, about 90 seconds, about 120 seconds, about 2.5 minutes, about 3 minutes, about 3.5 minutes, about 4 minutes, or about 5 minutes. In embodiments, where there are two or more mixing steps, the time intervals for each mixing can be the same (e.g., 2×10 seconds) or different (e.g., 10 seconds for first mixing and 20 seconds for second mixing). In any of the above embodiments, an enalapril liquid composition is allowed to stand for a period of time such as about 10 minutes, about 20 minutes, about 30 minutes, about 45 minutes, about 1 hour, about 1.5 hours or about 2 hours, to allow any air bubbles resultant from any of the mixing methods to dissipate.

Stability of Enalapril Oral Liquid Compositions

The enalapril oral liquid compositions described herein are stable in various storage conditions including refrigerated and ambient conditions. Stable as used herein refer to enalapril oral liquid compositions having at least about 90% enalapril and 5% or less total impurities or substances at the end of a given storage period. Stability is assessed by HPLC or any other known testing method. In some embodiments, the stable enalapril oral liquid compositions have about 5%, about 4%, about 3%, about 2.5%, about 2%, about 1.5%, about 1%, or about 0.5% total impurities or substances. In other embodiments, the stable enalapril oral liquid compositions have about 5% total impurities or substances. In yet other embodiments, the stable enalapril oral liquid compositions have about 4% total impurities or substances. In yet other embodiments, the stable enalapril oral liquid compositions have about 3% total impurities or substances. In yet other embodiments, the stable enalapril oral liquid compositions have about 2% total impurities or substances. In yet other embodiments, the stable enalapril oral liquid compositions have about 1% total impurities or substances. In further embodiments, the stable enalapril oral liquid compositions have at least about 90%, at least about 91%, at least about 92%, at least about 93%, or at least about 94% enalapril at the end of a given storage period.

At refrigerated and ambient conditions, in some embodiments, the enalapril oral liquid compositions described herein are stable for at least 1 week, 2 weeks, 4 weeks, 6 weeks, 8 weeks, 10 weeks, 12 weeks, 16 weeks, 20 weeks, at least 24 weeks, at least 30 weeks, or at least 36 weeks. In other embodiments, the enalapril oral liquid compositions described herein are stable at refrigerated and ambient conditions for at least 12 weeks. Ambient conditions include temperature and/or relative humidity (RH) that are at ambient levels (e.g. 25±5° C.; 55±10% RH). In some instances, an ambient condition is at about 20° C., about 21° C., about 22° C., about 23° C., about 24° C., about 25° C., about 26° C., about 27° C., about 28° C., about 29° C., or about 30° C. In other instances, an ambient condition is about 45% RH, about 50% RH, about 55% RH, about 60% RH or about 65% RH. Refrigerated conditions include temperature and/or relative humidity (RH) in typical refrigeration units (e.g., 5±3° C.). In some instances, a refrigerated condition is at about 2° C., about 3° C., about 4° C., about 5° C., about 6° C., about 7° C. or about 8° C. In other instances, a a refrigerated condition is at about 4° C.

In further embodiments, the stable enalapril oral liquid compositions described herein that are stored at ambient or refrigerated conditions for a give storage period after reconstitution provide similar, consistent or equivalent pharmacokinetic parameters as an enalapril oral liquid composition that is formulated prior to administration to a subject (i.e., freshly made). In other words, the enalapril oral liquid compositions described herein have stability after a storage period to provide similar, consistent or equivalent pharmacokinetic parameters as a freshly made enalapril oral liquid composition. For example, a 12 week stable enalapril oral liquid composition provides similar, consistent or equivalent pharmacokinetic parameters as an enalapril oral liquid composition made five minutes prior administration. Pharmacokinetic parameters include $C_{max}$, $T_{max}$, $AUC_{last}$, $AUC_{inf}$, $T_{1/2}$, $C_{last}$ for enalapril and/or enalaprilat and exemplary values are obtained and described in Example 7. In some instances, the stable enalapril oral liquid compositions described herein provide within 80% to 125%, 80% to 120%, 85% to 125%, 90% to 110% pharmacokinetic parameters of a freshly made enalapril oral liquid composition when the stable composition is stored at least 1 week, 2 weeks, 4 weeks, 6 weeks, 8 weeks, 10 weeks, 12 weeks, 16 weeks, 20 weeks, at least 24 weeks, at least 30 weeks, or at least 36 weeks after reconstitution. In other instances, the stable enalapril oral liquid compositions described herein provide within 80% to 125%, 80% to 120%, 85% to 125%, 90% to 110% pharmacokinetic parameters of a freshly made enalapril oral liquid composition when the stable composition is stored for 12 weeks after reconstitution.

Kits and Articles of Manufacture

For the enalapril powder and liquid compositions described herein, kits and articles of manufacture are also described. Such kits can comprise a carrier, package, or container that is compartmentalized to receive one or more containers such as vials, tubes, and the like, each of the container(s) comprising one of the separate elements to be used in a method described herein including an enalapril powder or liquid composition. Suitable containers include, for example, bottles, vials, syringes, and test tubes. The containers can be formed from a variety of materials such as glass or plastic.

A kit will typically may comprise one or more additional containers, each with one or more of various materials (such as reagents, optionally in concentrated form, and/or devices) desirable from a commercial and user standpoint for an enalapril powder or liquid composition described herein. Non-limiting examples of such materials include, but not limited to, buffers, diluents, filters, needles, syringes; carrier, package, container, vial and/or tube labels listing contents and/or instructions for use, and package inserts with instructions for use associated with an enalapril powder or liquid composition. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Methods

Provided herein, in one aspect, are methods of treatment comprising administration of the enalapril oral liquid compositions described herein to a subject. In some embodiments, the enalapril oral liquid compositions described herein treat hypertension in a subject. Hypertension as used herein includes both primary (essential) hypertension and secondary hypertension. In certain instances, hypertension is classified in cases when blood pressure values are greater than or equal to 140/90 (systolic/diastolic) mm Hg in a subject. In certain instances, the enalapril oral liquid compositions described herein treat a subject having a blood pressure values are greater than or equal to 140/90 mm Hg. In certain instances, the enalapril oral liquid compositions described herein treat primary (essential) hypertension in a subject. In other instances, the enalapril oral liquid compositions described herein treat secondary hypertension in a subject.

In other embodiments, the enalapril oral liquid compositions described herein treat prehypertension in a subject. Prehypertension as used herein refers to cases where a subject's blood pressure is elevated above normal but not to the level considered to be hypertension. In some instances, prehypertension is classified in cases when blood pressure values are 120-139/80-89 mm Hg. In certain instances, the enalapril oral liquid compositions described herein treat a subject having a blood pressure value of 120-139/80-89 mm Hg.

In yet other embodiments, the enalapril oral liquid compositions described herein are prophylactically administered to subjects suspected of having, predisposed to, or at risk of developing hypertension. In some embodiments, the administration of enalapril oral liquid compositions described herein allow for early intervention prior to onset of hypertension. In certain embodiments, upon detection of a biomarker, environmental, genetic factor, or other marker, the enalapril oral liquid compositions described herein are prophylactically administered to subjects.

In further embodiments, the enalapril oral liquid compositions described herein treat heart failure (e.g., symptomatic congestive), asymptomatic left ventricular dysfunction, myocardial infarction, diabetic nephropathy and chronic renal failure. In certain instances, the enalapril oral liquid compositions described herein treat symptomatic congestive heart failure. In other instances, the enalapril oral liquid compositions described herein treat asymptomatic left ventricular dysfunction. In further instances, the enalapril oral liquid compositions described herein treat myocardial infarction. In yet further instances, the enalapril oral liquid compositions described herein treat diabetic nephropathy. In yet further instances, the enalapril oral liquid compositions described herein treat chronic renal failure.

Dosing

In one aspect, the enalapril oral liquid compositions are used for the treatment of diseases and conditions described herein. In addition, a method for treating any of the diseases or conditions described herein in a subject in need of such treatment, involves administration of enalapril oral liquid compositions in therapeutically effective amounts to said subject.

Dosages of enalapril oral liquid compositions described can be determined by any suitable method. Maximum tolerated doses (MTD) and maximum response doses (MRD) for enalapril and/or enalaprilat can be determined via established animal and human experimental protocols as well as in the examples described herein. For example, toxicity and therapeutic efficacy of enalapril and/or enalaprilat can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Enalapril dosages exhibiting high therapeutic indices are of interest. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximal response or of maximum tolerated dose, are readily obtained via the protocols.

In some embodiments, the amount of a given enalapril oral liquid composition that corresponds to such an amount varies depending upon factors such as the particular enalapril salt or form, disease condition and its severity, the identity (e.g., age, weight, sex) of the subject or host in need of treatment, but can nevertheless be determined according to the particular circumstances surrounding the case, including, e.g., the specific agent being administered, the liquid composition type, the condition being treated, and the subject or host being treated.

In some embodiments, the enalapril oral liquid compositions described herein are provided in a dose per day from about 0.01 mg to 100 mg, from about 0.1 mg to about 80 mg, from about 1 to about 60, from about 2 mg to about 40 mg of enalapril. In certain embodiments, the enalapril oral liquid compositions described herein are provided in a daily dose of about 0.01 mg, about 0.05 mg, about 0.1 mg, about 0.2 mg, about 0.4 mg, about 0.6 mg, about 0.8 mg, about 1 mg, about 1.5 mg, about 2 mg, about 2.5 mg, about 3 mg, about 4 mg, about 5 mg, about 6 mg, about 7 mg, about 8 mg, about 9 mg, about 10 mg, about 11 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 76, mg, about 80 mg, about 85 mg, about 90 mg or about 100 mg, or any range derivable therein. In certain instances, the enalapril oral liquid compositions described herein are provided in a dose per day of about 1 mg. In certain instances, the enalapril oral liquid compositions described herein are provided in a dose per day of about 2 mg. In certain instances, the enalapril oral liquid compositions described herein are provided in a dose per day of about 3 mg. In certain instances, the enalapril oral liquid compositions described herein are provided in a dose per day of about 4 mg. In certain instances, the enalapril oral liquid compositions described herein are provided in a dose per day of about 5 mg. In certain instances, the enalapril oral liquid compositions described herein are provided in a dose per day of about 6 mg. In certain instances, the enalapril oral liquid compositions described herein are provided in a dose per day of about 7 mg. In certain instances, the enalapril oral liquid compositions described herein are provided in a dose per day of about 8 mg. In certain instances, the enalapril oral liquid compositions described herein are provided in a dose per day of about 9 mg. In certain instances, the enalapril oral liquid compositions described herein are provided in a dose per day of about 10 mg. In certain instances, the enalapril oral liquid compositions described herein are provided in a dose per day of about 11 mg. In certain instances, the enalapril oral liquid compositions described herein are provided in a dose per day of about 12 mg. The dose per day described herein can be given once per day or multiple times per day in the form of sub-doses given b.i.d., t.i.d., q.i.d., or the like where the number of sub-doses equal the dose per day.

In further embodiments, the daily dosages appropriate for the enalapril oral liquid compositions described herein are from about 0.01 to about 1.0 mg/kg per body weight. In one embodiment, the daily dosages appropriate for the enalapril oral liquid compositions are from about 0.02 to about 0.8 mg/kg enalapril per body weight. In another embodiment, the daily dosage appropriate for the enalapril oral liquid compositions are from about 0.05 to about 0.6 mg/kg per body weight. In another embodiment, the daily dosage appropriate for the enalapril oral liquid compositions is about 0.05 mg/kg, about 0.06 mg/kg, about 0.07 mg/kg, about 0.08 mg/kg, about 0.10 mg/kg, about 0.15 mg/kg, about 0.20 mg/kg, about 0.25 mg/kg, about 0.30 mg/kg, about 0.40 mg/kg, about 0.50 mg/kg, or about 0.60 mg/kg. In a further embodiment, the daily dosage appropriate for the enalapril oral liquid compositions is about 0.08 mg/kg.

In other embodiments the enalapril oral liquid compositions are provided at the maximum tolerated dose (MTD) for enalapril and/or enalaprilat. In other embodiments, the amount of the enalapril oral liquid compositions administered is from about 10% to about 90% of the maximum tolerated dose (MTD), from about 25% to about 75% of the MTD, or about 50% of the MTD. In particular embodiments, the amount of the enalapril oral liquid compositions administered is from about 5%, 10%, 15%, 20%, 25%, 30%, 35%, 40%, 45%, 50%, 55%, 60%, 65%, 70%, 75%, 80%, 85%, 90%, 95%, 99%, or higher, or any range derivable therein, of the MTD for enalapril and/or enalaprilat.

In further embodiments, the enalapril oral liquid compositions are provided in a dosage that is similar, comparable or equivalent to a dosage of a known enalapril tablet formulation. In other embodiments, the enalapril oral liquid compositions are provided in a dosage that provides a similar, comparable or equivalent pharmacokinetic parameters (e.g., AUC, $C_{max}$, $T_{max}$, $C_{min}$, $T_{1/2}$) as a dosage of a known enalapril tablet formulation. Similar, comparable or equivalent pharmacokinetic parameters, in some instances, refer to within 80% to 125%, 80% to 120%, 85% to 125%, 90% to 110%, or increments therein, of the given values. It should be recognized that the ranges can, but need not be symmetrical, e.g., 85% to 105%.

Administration

Administration of a enalapril oral liquid composition is at a dosage described herein or at other dose levels and compositions determined and contemplated by a medical practitioner. In certain embodiments, the enalapril oral liquid compositions described herein are administered for prophylactic and/or therapeutic treatments. In certain therapeutic applications, the enalapril oral liquid compositions are administered to a patient already suffering from a disease, e.g., hypertension, in an amount sufficient to cure the disease or at least partially arrest or ameliorate the symptoms, e.g., lower blood pressure. Amounts effective for this use depend on the age of the patient, severity of the disease, previous therapy, the patient's health status, weight, and response to the enalapril compositions, and the judgment of the treating physician. Therapeutically effective amounts are optionally determined by methods including, but not limited to, a dose escalation clinical trial.

In prophylactic applications, the enalapril oral liquid compositions described herein are administered to a patient susceptible to or otherwise at risk of a particular disease, e.g., hypertension. Such an amount is defined to be a "prophylactically effective amount or dose." In this use, the precise amounts also depend on the patient's age, state of health, weight, and the like. When used in a patient, effective amounts for this use will depend on the risk or susceptibility of developing the particular disease, previous therapy, the patient's health status and response to the enalapril compositions, and the judgment of the treating physician.

In certain embodiments wherein the patient's condition does not improve, upon the doctor's discretion the administration of an enalapril oral liquid composition described herein are administered chronically, that is, for an extended period of time, including throughout the duration of the patient's life in order to ameliorate or otherwise control or limit the symptoms of the patient's disease. In other embodiments, administration of an enalapril oral liquid composition continues until complete or partial response of a disease.

In certain embodiments wherein a patient's status does improve, the dose of an enalapril oral liquid composition being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, enalapril oral liquid compositions described herein are administered chronically. For example, in some embodiments, an enalapril oral liquid composition is administered as a continuous dose, i.e., administered daily to a subject. In some other embodiments, enalapril oral liquid compositions described herein are administered intermittently (e.g. drug holiday that includes a period of time in which the composition is not administered or is administered in a reduced amount).

In some embodiments an enalapril oral liquid composition is administered to a subject who is in a fasted state. A fasted state refers to a subject who has gone without food or fasted for a certain period of time. General fasting periods include at least 4 hours, at least 6 hours, at least 8 hours, at least 10 hours, at least 12 hours, at least 14 hours and at least 16 hours without food. In some embodiments, an enalapril oral liquid composition is administered orally to a subject who is in a fasted state for at least 8 hours. In other embodiments, an enalapril oral liquid composition is administered to a subject who is in a fasted state for at least 10 hours. In yet other embodiments, an enalapril oral liquid composition is administered to a subject who is in a fasted state for at least 12 hours. In other embodiments, an enalapril oral liquid composition is administered to a subject who has fasted overnight.

In other embodiments an enalapril oral liquid composition is administered to a subject who is in a fed state. A fed state refers to a subject who has taken food or has had a meal. In certain embodiments, an enalapril oral liquid composition is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, or 2 hours post-meal. In certain instances, an enalapril oral liquid composition is administered to a subject in a fed state 30 minutes post-meal. In other instances, an enalapril oral liquid composition is administered to a subject in a fed state 1 hour post-meal. In yet further embodiments, an enalapril oral liquid composition is administered to a subject with food.

In further embodiments described herein, an enalapril oral liquid composition is administered at a certain time of day for the entire administration period. For example, an enalapril oral liquid composition can be administered at a certain time in the morning, in the evening, or prior to bed. In certain instances, an enalapril oral liquid composition is administered in the morning. In other embodiments, an enalapril oral liquid composition can be administered at different times of the day for the entire administration period. For example, an enalapril oral liquid composition can be administered on 8:00 am in the morning for the first day, 12 pm noon for the next day or administration, 4 pm in the afternoon for the third day or administration, and so on.

Further Combinations

The treatment of certain diseases or conditions (e.g., hypertension, heart failure, myocardial infarction and the like) in a subject with an enalapril oral liquid composition described herein encompass additional therapies and treatment regimens with other agents in some embodiments. Such additional therapies and treatment regimens can include another therapy, e.g., additional anti-hypertensives, for treatment of the particular disease or condition in some embodiments. Alternatively, in other embodiments, additional therapies and treatment regimens include other agents used to treat adjunct conditions associated with the disease or condition or a side effect from the enalapril oral liquid composition in the therapy.

Additional agents for use in combination with an enalapril oral liquid composition described herein include, but are not limited to, diuretics (loop, thiazide, potassium-sparing, and the like), beta blockers (metoprolol, propanolol, pronethalol, and the like), alpha blockers (phentolamine, phenoxybenzamine, tamsulosin, prazosin, and the like), mixed alpha and beta blockers (bucindolol, carvedilol, labetalol), calcium channel blockers (dihydropyridines such as nifedipine, amlodipine, etc., dilitazem, verapamil and the like), angiotensin II receptor antagonists (saralasin, lsartan, eprosartin, irbesartan, valsartan, and the like), other ACE inhibitors (captopril, quinapril, ramipril, lisinopril, zofenopril, and the like), aldosterone antagonists (eplerenone, spironolactone and the like), vasodilators (hydralazine and the like) and alpha-2 agonists (clonidine, moxonidine, guanabenz and the like).

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as enalapril is directed to the treatment and/or the amelioration of, reversal of, or stabilization of the symptoms of hypertension described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with an enalapril composition, can include, but is not limited to, providing an enalapril composition into or onto the target tissue; providing an enalapril composition systemically to a patient by, e.g., oral administration whereby the therapeutic reaches the target tissue or cells. "Administering" a composition may be accomplished by injection, topical administration, and oral administration or by other methods alone or in combination with other known techniques.

The term "animal" as used herein includes, but is not limited to, humans and non-human vertebrates such as wild, domestic and farm animals. As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In further instances, the human is under the age of 12 years. In certain instances, the human is elderly. In other instances, the human is 60 years of age or older. Other examples of subjects include experimental animals such as mice, rats, dogs, cats, goats, sheep, pigs, and cows. The experimental animal can be an animal model for a disorder, e.g., a transgenic mouse with hypertensive pathology. A patient can be a human suffering from hypertension, or its variants or etiological forms.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a composition of the present disclosure may be used to inhibit, block, or reverse the activation, migration, or proliferation of cells or to effectively treat hypertension or ameliorate the symptoms of hypertension.

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

EXAMPLES

Example 1: Stability of Enalapril Formulated Powder

Enalapril Powder Formulation: The stability of enalapril with lactose, sucrose or mannitol was assessed in various storage conditions. 2% w/w enalapril powder was formulated via granulation according to the following table.

| Component | Amount in 150 mL Bottle (mg) | Weight (% w/w solids) | Batch (g) |
|---|---|---|---|
| Enalapril Maleate | 150 | 2.0 | 6.000 |
| Stability Agent (Lactose, Sucrose or Mannitol) | 7350 | 98.0 | 294.0 |
| Sodium Bicarbonate | — | — | 3.074 |
| Water | — | — | 25.00 |
| Total Solids | 7500 | 100.0 | 300.0 |

Enalapril Maleate was slowly dissolved in a 12% sodium bicarbonate solution. The stability agent (lactose, sucrose or mannitol) was mixed in a mixer at slow speed and the enalapril solution was slowly sprayed onto the stability agent over a period of about 20 minutes. The wetted material was spread onto a dish and placed in a 60° C. oven for at least 4 h. The dried granulation was passed through a 40-mesh screen.

Stability Studies: The effect of the three stability agents, lactose, mannitol and sucrose on the stability of the granulated powder was evaluated. 7.5 g of powder was placed in 8 oz amber, graduated PET bottles and stored under refrigerated, 25° C./60% Relative Humidity (RH), 40° C./ambient and 60° C./ambient conditions. At various time points the powder in the bottle was analyzed for enalapril by HPLC/UV analysis. The following tables depict the stability of enalapril+stability agent powder in bottle in the various storage conditions.

| 2% w/w Enalapril/Lactose Powder in Bottle Formulation | | | | |
|---|---|---|---|---|
| Time (Weeks) | Refrigerated | 25° C./ 60% RH | 40° C./ ambient | 60° C./ ambient |
| 0 | 101.54 | 101.54 | 101.54 | 101.54 |
| 1 | 100.27 | 100.59 | 98.61 | 94.74 |
| 2 | 100.37 | 100.60 | 98.82 | 94.51 |
| 3 | 101.10 | 99.58 | 98.45 | 93.44 |
| 4 | 99.03 | 98.53 | 96.94 | 92.66 |
| 8 | 100.23 | 99.63 | 98.89 | 90.56 |
| 12 | 102.20 | 99.53 | 100.02 | 89.76 |
| 26 | 101.28 | 95.83 | 97.89 | 75.57 |
| 52 | 101.50 | 91.90 | 93.70 | N/A |

| 2% w/w Enalapril/Mannitol Powder in Bottle Formulation | | | | |
|---|---|---|---|---|
| Time (Weeks) | Refrigerated | 25° C./ 60% RH | 40° C./ ambient | 60° C./ ambient |
| 0 | 100.16 | 100.16 | 100.16 | 100.16 |
| 1 | 99.61 | 99.57 | 93.42 | 96.96 |
| 2 | 98.56 | 98.41 | 94.41 | 101.14 |
| 3 | 99.21 | 98.51 | 99.42 | 101.24 |
| 4 | 99.20 | 98.59 | 101.26 | 99.97 |
| 8 | 101.26 | 98.88 | 102.17 | 100.80 |
| 12 | 103.33 | 99.67 | 103.31 | 95.15 |
| 26 | 102.19 | 96.89 | 102.68 | 94.66 |
| 52 | 102.50 | 94.30 | 99.70 | N/A |

| 2% w/w Enalapril/Sucrose Powder in Bottle Formulation | | | | |
|---|---|---|---|---|
| Time (Weeks) | Refrigerated | 25° C./ 60% RH | 40° C./ ambient | 60° C./ ambient |
| 0 | 98.68 | 98.68 | 98.68 | 98.68 |
| 2 | 97.67 | 100.60 | 98.87 | 99.92 |
| 4 | 97.40 | 100.50 | 98.97 | 99.06 |

-continued

| 2% w/w Enalapril/Sucrose Powder in Bottle Formulation | | | | |
|---|---|---|---|---|
| Time (Weeks) | Refrigerated | 25° C./60% RH | 40° C./ambient | 60° C./ambient |
| 8 | 98.40 | 99.56 | 98.83 | 97.74 |
| 12 | 97.17 | 98.47 | 97.13 | 94.97 |
| 26 | 97.90 | 96.40 | 99.00 | 93.50 |
| 52 | N/A | N/A | N/A | N/A |

Based on the powder in bottle stability at accelerated conditions (25° C./60% RH, 40° C./ambient, 60° C./ambient), it was determined that the enalapril/mannitol formulation was the most stable.

Example 2: Stability of Prepared Enalapril Solution

Enalapril Solution Formulation: 1.0 mg/mL enalapril solutions were prepared from the lactose and mannitol granulations (Example 1) made with the addition of OraSweet SF® flavored syrup and placed under refrigerated, 25° C./60% RH and 40° C./ambient conditions. A enalapril/sucrose solution was prepared at 2 mg/mL concentration to evaluate the effect of the higher concentration on solution stability. The following tables depict the stability of enalapril+stability agent solution in the various storage conditions.

| 1 mg/mL Enalapril/Lactose Prepared Solution | | | |
|---|---|---|---|
| Time (Weeks) | Refrigerated | 25° C./60% RH | 40° C./ambient |
| 0 | 101.66 | 101.66 | 101.66 |
| 1 | 100.63 | 100.33 | 97.18 |
| 2 | 101.35 | 99.77 | 93.69 |
| 3 | 101.25 | 98.68 | 90.03 |
| 4 | 100.65 | 97.25 | 86.21 |
| 8 | 101.27 | 94.19 | 73.69 |
| 12 | 102.15 | 92.99 | 65.91 |

| 1 mg/mL Enalapril/Mannitol Prepared Solution | | | |
|---|---|---|---|
| Time (Weeks) | Refrigerated | 25° C./60% RH | 40° C./ambient |
| 0 | 95.86 | 95.86 | 95.86 |
| 1 | 94.56 | 94.08 | 91.28 |
| 2 | 94.98 | 93.90 | 87.48 |
| 3 | 95.06 | 92.59 | 83.86 |
| 4 | 94.42 | 91.28 | 80.45 |
| 8 | 95.10 | 88.39 | 68.52 |
| 12 | 95.74 | 86.99 | 60.43 |

| 2 mg/mL Enalapril/Sucrose Prepared Solution | | | |
|---|---|---|---|
| Time (Weeks) | Refrigerated | 25° C./60% RH | 40° C./ambient |
| 0 | 99.16 | 99.16 | 99.16 |
| 2 | 101.1 | 98.71 | 89.05 |
| 4 | 101.3 | 95.48 | 79.86 |
| 8 | 99.79 | 90.35 | 62.94 |
| 12 | 99.40 | 86.18 | 40.24 |

In the prepared solutions, the enalapril+mannitol solution was most stable at 40° C./ambient conditions.

Example 3: Direct Blend Enalapril Powder Compositions

Enalapril Powder Composition A: An enalapril powder composition as set forth in the following table is prepared.

| Component | Amount in 150 mL Bottle (mg) | Weight (% w/w solids) |
|---|---|---|
| Enalapril Maleate | 150 | 14.29 |
| Mannitol | 900 | 85.71 |
| Total Solids | 1050 | 100.0 |

The composition is prepared by adding the components together. The powder is then screened and direct blended until blend uniformity.

Enalapril Powder Composition B: An enalapril powder composition as set forth in the following table is prepared.

| Component | Amount in 150 mL Bottle (mg) | Weight (% w/w solids) |
|---|---|---|
| Enalapril Maleate | 150 | 14.29 |
| Mannitol | 890 | 84.76 |
| Colloidal Silicon Dioxide | 10 | 0.95 |
| Total Solids | 1050 | 100.0 |

The composition is prepared by adding the components together. The powder is then screened and direct blended until blend uniformity.

Enalapril Powder Composition C: An enalapril powder composition as set forth in the following table is prepared.

| Component | Amount in 150 mL Bottle (mg) | Weight (% w/w solids) |
|---|---|---|
| Enalapril Maleate | 150 | 14.29 |
| Mannitol | 590 | 56.19 |
| Colloidal Silicon Dioxide | 10 | 0.95 |
| Sorbitol | 300 | 28.57 |
| Total Solids | 1050 | 100.0 |

The composition is prepared by adding the components together. The powder is then screened and direct blended until blend uniformity.

Enalapril Powder Composition D: An enalapril powder composition as set forth in the following table is prepared.

| Component | Amount in 150 mL Bottle (mg) | Weight (% w/w solids) |
|---|---|---|
| Enalapril Maleate | 150 | 12.5 |
| Mannitol | 590 | 49.17 |
| Colloidal Silicon Dioxide | 10 | 0.83 |
| Sorbitol | 300 | 25.0 |
| Wild Cherry Flavor | 150 | 12.5 |
| Total Solids | 1200 | 100.0 |

Enalapril Powder Composition E: An enalapril powder composition as set forth in the following table is prepared.

| Component | Amount in 150 mL Bottle (mg) | Weight (% w/w solids) |
|---|---|---|
| Enalapril Maleate | 150 | 7.5 |
| Mannitol | 590 | 29.5 |
| Colloidal Silicon Dioxide | 10 | 0.5 |
| Sorbitol | 300 | 15 |
| Sodium Bicarbonate | 800 | 40 |
| Lemon Flavor | 150 | 7.5 |
| Total Solids | 2000 | 100.0 |

Example 4: Enalapril Composition Scale-Up Optimization Studies

Scale-up studies investigated blend and bottle content uniformity

Blend and Bottle Content Uniformity of Enalapril Powder Composition A: Enalapril Powder Composition A (150 mg enalapril, 900 mg mannitol/bottle) was scaled-up and the resultant formulation tested for blend and content uniformity. For blend uniformity, 10 lg samples were taken from the blender (top front right, middle front right, bottom front, top front left, middle front left, top back right, middle back right, bottom back, top back left, and middle back left) by a suitable powder sampler at the below times.

| Blend Uniformity - Enalapril Powder Composition A | | |
|---|---|---|
| Blending Time (min) | Avg drug assay (%) | % RSD |
| 10 | 96.0 | 2.80 |
| 15 | 96.6 | 2.13 |
| 20 | 99.5 | 3.69 |

Bottle content uniformity values were assessed via a hopper study after filling and capping the Enalapril Powder Composition blend into 150 mL bottles:

| Bottle Content Uniformity - Enalapril Powder Composition A | | | |
|---|---|---|---|
| Time Point | Avg drug assay (%) | % RSD | Ace. Value (Limit ≤15) |
| Beginning | 89.9 | 2.12 | 13.2 |
| Middle | 104.7 | 2.66 | 9.9 |
| End | 99.8 | 3.14 | 7.5 |

The content uniformity study revealed that some segregation of the powder composition could have occurred post-blending.

Blend Time Variation for Enalapril Powder Composition A: Blend time was assessed for possibility of contributing to segregation of the powder composition. Blend time was shortened to 5 minutes and blend uniformity and bottle content uniformity was assessed as above:

| Blend Uniformity - Enalapril Powder Composition A | | |
|---|---|---|
| Blending Time (min) | Avg drug assay (%) | % RSD |
| 5 | 96.7 | 1.25 |

| Bottle Content Uniformity - Enalapril Powder Composition A | | |
|---|---|---|
| Study | Avg drug assay (%) | % RSD |
| Content Uniformity | 95.9 | 6.14 |
| By Weight | 97.7 | 6.69 |

The high % RSD was observed in the bottle content uniformity studies indicating variance in the filling and capping of the drug powder composition.

Blend time was changed back to 10 minutes in an attempt to optimize blend and fill, however, it was not successful.

Lengthening the blend time to 20, 30, 40 and 60 minutes revealed the following observations:

| Blend Uniformity - Enalapril Powder Composition A | | |
|---|---|---|
| Blending Time (min) | Visual Observation | Avg drug assay (%) |
| 20 | Homogenous | 89.9, 102.8, 96.1 |
| 30 | Small round balls segregating in blend | 90.4, 90.1, 100.9 |
| 40 | Small round balls segregating in blend and gradually increasing in proportion | 105.4 |
| 60 | Much greater and clear segregation of round balls in the blend | 139.8; fines: 55.8 |

FIG. 1 shows a visual depiction of the enalapril powder composition A blended for 60 minutes. Thus, a lower blend time (e.g., about 10-20 minutes) is contemplated to be more optimal to prevent 'balling up' and segregation of the powder blend.

Figure 2A:
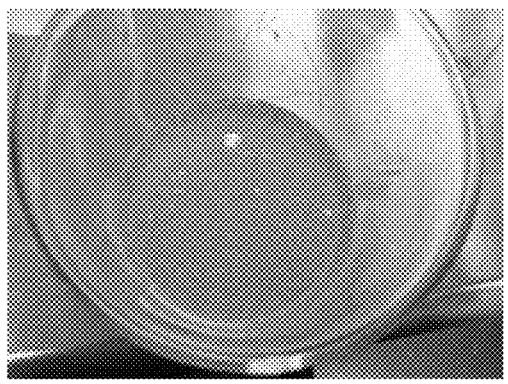
FIG. 2A: enalapril and mannitol.

The scaled-up enalapril and mannitol powder compositions (Enalapril Powder Composition A and the like) were examined in reconstitution studies where 150 mL Ora-Sweet® SF sugar-free flavored syrup was to the powder compositions. Scaled-up enalapril and mannitol powder compositions such as Enalapril Powder Composition A did not dissolve in the syrup, but instead resulted in powder clumping and specking on the surface of the liquid, termed 'clouding'. Various enalapril and mannitol formulations were examined at different concentrations, which resulted in similar 'clouding'. FIG. 2A shows the clouding phenomenon from an exemplary enalapril and mannitol powder formulation.

Figure 2B:
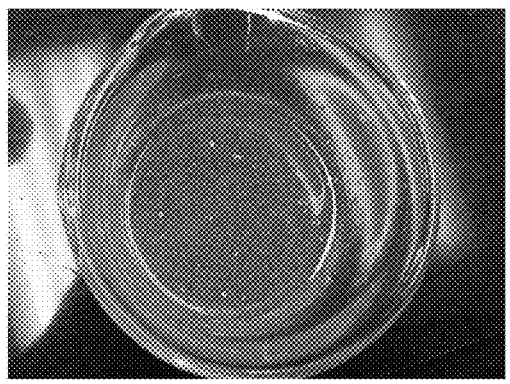
FIG. 2B: neat enalapril.

Reconstitution of Neat Enalapril Powder in Bottle: Due to the 'clouding' in the reconstitution as well as the uniformity issues in the scale-up studies of Enalapril Powder Composition A, neat enalapril, i.e., drug alone, without any excipients, was examined for scale-up bottle filling and subsequent reconstitution. It was observed that during reconstitution with 150 mL Ora-Sweet® SF sugar-free flavored syrup, the neat enalapril did not dissolve but floated on the surface of the liquid, even after 2 hours standing after reconstitution (FIG. 2B).

Colloidal Silicon Dioxide Addition to Form Enalapril Powder Composition B:

Although colloidal silicon dioxide has been reported to decrease stability of enalapril (Rezende et al., Stability and Compatibility Study on Enalapril Maleate using Thermoanalytical Techniques, *J. Thermal Anal. & calorimetry*, 2008 (93) 881-886), the addition of colloidal silicon dioxide to an enalapril powder composition during scale-up resulted in improved and acceptable blend uniformity and bottle content uniformity levels. Enalapril Powder Composition B (150 mg enalapril, 890 mg mannitol, 10 mg colloidal silicon dioxide/bottle) was scaled-up and the resultant formulation tested for blend and content uniformity as described above. The blend and content uniformity assays showed that the addition of colloidal silicon dioxide imparted uniformity in the powder composition:

| Blend Uniformity - Enalapril Powder Composition B | | |
| --- | --- | --- |
| Blending Time (min) | Avg drug assay (%) | % RSD |
| 10 | 99.8 | 1.34 |
| 10 | 99.7 | 1.08 |

| Bottle Content Uniformity - Enalapril Powder Composition B | | |
| --- | --- | --- |
| Study | Avg drug assay (%) | % RSD |
| Content Uniformity | 102.6 | 1.98 |
| Content Uniformity | 98.5 | 2.77 |

Figure 2C:
FIG. 2C: enalapril, mannitol and colloidal silicon dioxide.

In reconstitution studies, surprisingly, the addition of colloidal silicon dioxide resulted in a solution that, upon visual inspection, was truly dissolved and homogenous (FIG. 2C).

A lower amount of colloidal silicon dioxide was also studied (150 mg enalapril, 895 mg mannitol, 5 mg colloidal silicon dioxide/bottle). However the enalapril powder composition had lower flowability than that of enalapril powder composition B.

The stability of the enalapril powder and liquid composition with respect to the addition of colloidal silicon dioxide was analyzed in Example 6.

Example 5: Additional Reconstitution Methods and Studies

The overall mixing efficiency and solution/suspension drug concentration homogeneity was evaluated over a series of mixing methods and times.

Mixing Method A: 75 mL of Ora-Sweet® SF sugar-free flavored syrup was added to a 150 mL bottle of Enalapril Powder Composition B and the bottle was shaken vigorously. A second 75 mL of Ora-Sweet® SF syrup was subsequently added and the bottle was shaken vigorously.

Observations: The resultant liquid contained entrapped air bubbles. It was determined that the bubbles would interfere with dosing as a variable volume of the liquid could be administered in dosing syringes for administration.

Mixing Method B: 75 mL of Ora-Sweet® SF sugar-free flavored syrup was added to a 150 mL bottle of Enalapril Powder Composition B and the bottle was gently swirled. A second 75 mL of Ora-Sweet® SF syrup was subsequently added and the bottle was gently swirled. The bottle was then inverted slowly for about 5 times.

Observations: The gently swirling and subsequent inversions minimized the bubble formation. However, in a clinical trial similar to Example 7, it was observed that the subjects had received a lower dose (about 1.30 mg) of enalapril rather than standard 10 mg dosage. Based on this observation, it was determined that the mixing method did not introduce enough energy in the process and resulted in improper wetting and mixing of the powder.

Mixing Method C: 150 mL bottle of Enalapril Powder Composition B was first tapped on a hard surface to disperse any powder caking. 75 mL of Ora-Sweet® SF sugar-free flavored syrup was added to the 150 mL bottle and the bottle was shaken for specified time intervals (10, 20, 30, 45 and 60 seconds). A second 75 mL of Ora-Sweet® SF syrup was subsequently added and the bottle was shaken for the specified time interval. Bubbles were allowed to dissipate (for at least one hour). Two samples were taken immediately after the second shaking. One sample was filtered through a 0.45 micron filter. A third sample was taken 1 h after the second shaking and after any bubbles dissipated from the liquid. The three samples were assayed by HPLC. The mixing and homogeneity results are as follows:

| Mixing Method C: Enalapril by HPLC as % of 1 mg/mL | | | |
| --- | --- | --- | --- |
| Time (seconds) | Sample 1 (unfiltered) | Sample 2 (filtered) | Sample 3 (1 h) |
| 2 × 10 | 101.3 | 101.2 | 101.2 |
| 2 × 20 | 100.9 | 100.8 | 100.8 |
| 2 × 30 | 101.5 | 101.3 | 101.1 |
| 2 × 45 | 101.6 | 101.7 | 101.7 |
| 2 × 60 | 100.9 | 100.9 | 101.1 |

Observations: There was no perceived difference observed between filtered and unfiltered samples indicating that the reconstituted enalapril liquid is not a suspension. The addition of 75 mL of Ora-Sweet® SF syrup followed by shaking for 10 seconds and the addition of another 75 mL of Ora-Sweet® SF syrup followed by shaking for 10 seconds resulted in a homogenous solution. All longer shaking times produced equivalent results.

Example 6: Additional Stability Studies

Powder Stability: Enalapril Powder Composition B and its reconstituted oral liquid form were further investigated in stability studies. 1050 mg enalapril Powder Composition B in 150 mL white plastic bottles were examined for stability in 25±2° C./60±5% RH at up to 9 months and 40±2° C./75±5% RH (accelerated) conditions at up to 6 months. At each given time point, enalapril and related substances were assayed via HPLC. The below tables depict stability of the powder at the various conditions.

| Enalapril Powder Composition B - 25° C./60% RH | | | |
| --- | --- | --- | --- |
| Time (Months) | Enalapril (%) | Enalaprilat (%) | DKP (%) |
| 0 | 97.8 | 0.05 | 0.02 |
| 1 | 98.6 | 0.05 | 0.03 |
| 2 | 97.6 | 0.12 | 0.05 |
| 3 | 98.6 | 0.06 | 0.07 |
| 6 | 96.8 | 0.09 | 0.11 |
| 9 | 98.6 | 0.12 | 0.15 |

| Enalapril Powder Composition B - 40° C./75% RH | | | |
| --- | --- | --- | --- |
| Time (Months) | Enalapril (%) | Enalaprilat (%) | DKP (%) |
| 0 | 97.8 | 0.05 | 0.2 |
| 1 | 97.9 | 0.12 | 0.23 |

-continued

Enalapril Powder Composition B - 40° C./75% RH

| Time (Months) | Enalapril (%) | Enalaprilat (%) | DKP (%) |
|---|---|---|---|
| 2 | 96.8 | 0.15 | 0.32 |
| 3 | 97.2 | 0.16 | 0.42 |
| 6 | 96.2 | 0.18 | 0.63 |

Enalapril Powder Composition B remained stable through 6 months under accelerated stability conditions and 9 months under ambient (25±2° C./60±5% RH) conditions at up to 9 months conditions with slight increase in the levels of enalaprilat and DPK. However, none of the total related impurities exceeded 5%. Stability at ambient conditions was also examined for two additional lots of Enalapril Powder Composition B. Similar results were observed for the levels of enalaprilat and DPK.

Reconstituted Liquid Stability: Enalapril Powder Composition B was reconstituted in 150 mL bottles according to Mixing Method C (2×30 s of shaking) and stored at ambient conditions. Aliquots were taken during selected time points during the study period. The below tables depict stability of the reconstituted liquid at the various conditions.

Enalapril Reconstituted Liquid - Ambient

| Time (Weeks) | Enalapril (%) | Enalaprilat (%) | DKP (%) |
|---|---|---|---|
| 0 | 97.4 | 0.43 | 0.04 |
| 2 | 96.8 | 0.73 | 0.08 |
| 4 | 96.9 | 0.87 | 0.08 |
| 8 | 95.4 | 1.35 | 0.12 |
| 12 | 93.7 | 2.22 | 0.17 |

After being reconstituted, the enalapril liquid was stable in ambient conditions with essentially unchanged values of its attributes, including microbial limits, preservative effectiveness and preservative assay up to the end of the study period (12 weeks).

Example 7: Clinical Trial: Bioavailability Study of 10 mg Enalapril Maleate Oral Liquid Vs Vasotec® 10 mg Tablets Under Fasted Conditions and 10 mg Enalapril Maleate Oral Liquid in Fed Conditions in Healthy Adults The objectives of this single-dose, open-label, randomized, three-period, three-treatment, three-way crossover study were:
To assess the bioavailability of a test formulation of 10 mg oral liquid reconstituted from Enalapril Powder Composition B versus Vasotec® 10 mg enalapril tablets under fasted conditions in healthy adults
To assess the food effect on a test formulation of 10 mg oral liquid reconstituted from Enalapril Powder Composition B in healthy adults
Study Design: Healthy adult subjects were to receive each of the following three treatments in a randomized fashion during three study periods:
Treatment A, Test Formulation: Enalapril maleate oral liquid reconstituted from Enalapril Powder Composition B via Mixing Method C (2×30 s of shaking), 10 mg/10 mL, administered under fasted conditions
Treatment B, Reference Product: Vasotec®, one 10 mg tablet, administered under fasted conditions
Treatment C, Test Formulation: Enalapril maleate oral liquid reconstituted from Enalapril Powder Composition B via Mixing Method C (2×30 s of shaking), 10 mg/10 mL, administered under fed conditions Screening assessments were performed by the investigator or designee within 28 days prior to study start. Treatments A and B were to be administered after an overnight fast of at least 10 hours; Treatment C was to be administered following an overnight fast of at least 10 hours and an FDA standard high-calorie, high-fat breakfast meal beginning 30 minutes prior to administration of the study drug. Each dose was to be orally administered with 240 mL (8 fl. oz.) of room temperature tap water; after dosing, no food was allowed until 4 hours postdose. Each drug administration was separated by a washout period of ≥7 days.

During each study period, meals were the same and scheduled at approximately the same times relative to dose. In addition, during each period, blood samples were obtained prior to and following each dose at selected times through 72 hours postdose. Plasma pharmacokinetic (PK) samples were analyzed for enalapril and enalaprilat using a validated analytical method; appropriate PK parameters were calculated for each formulation using on-compartmental methods. Blood was also drawn and urine collected for clinical laboratory testing at screening and at the end of the study.

Each subject was to receive a total of three single doses, one dose at each of three study periods; the duration of the study for each subject would be approximately 45 days.

Subject Criteria: Subjects must have been a male or non-pregnant, non-breastfeeding female; 18 to 55 years of age; with body mass index (BMI) between 18 and 30 kg/m$^2$ and weight a minimum of 50 kg (110 lbs). Subjects were not to have a history or presence of clinically significant cardiovascular, pulmonary, hepatic, renal, hematologic, gastrointestinal, endocrine, immunologic, dermatologic, neurologic, oncologic, or psychiatric disease, or any other condition that, in the opinion of the investigator, would jeopardize the safety of the subject or the validity of the study results; and were not to have a history of chronic cough, hyperkalemia, renal insufficiency, renal artery stenosis, or angioedema related to previous treatment with an angiotensin-converting enzyme inhibitor.

Results

Various pharmacokinetic parameters are summarized below for enalapril and enalaprilat.

Mean PK Parameters Single 10 mg Doses

| $C_{max}$ (ng/mL) | $T_{max}$ (h) | $AUC_{last}$ (h*ng/mL) | $AUC_{inf}$ (h*ng/mL) | $T_{1/2}$ (h) | $C_{last}$ (ng/mL) |
|---|---|---|---|---|---|
| Treatment A - Enalapril | | | | | |
| 58.0 | 0.87 | 102.6 | 103.7 | 1.70 | 0.460 |
| Treatment B - Enalapril | | | | | |
| 61.8 | 0.92 | 106.5 | 107.5 | 1.45 | 0.467 |
| Treatment C - Enalapril | | | | | |
| 31.3 | 1.21 | 88.47 | 88.70 | 1.34 | 0.507 |
| Treatment A - Enalaprilat | | | | | |
| 41.0 | 3.45 | 405.3 | 443.3 | 30.49 | 0.841 |

-continued

| Mean PK Parameters Single 10 mg Doses | | | | | |
|---|---|---|---|---|---|
| $C_{max}$ (ng/mL) | $T_{max}$ (h) | $AUC_{last}$ (h*ng/mL) | $AUC_{inf}$ (h*ng/mL) | $T_{1/2}$ (h) | $C_{last}$ (ng/mL) |
| Treatment B - Enalaprilat | | | | | |
| 44.5 | 3.51 | 417.1 | 455.9 | 30.78 | 0.860 |
| Treatment C - Enalaprilat | | | | | |
| 26.4 | 4.49 | 315.7 | 360.1 | 33.94 | 0.889 |

Figure 3:
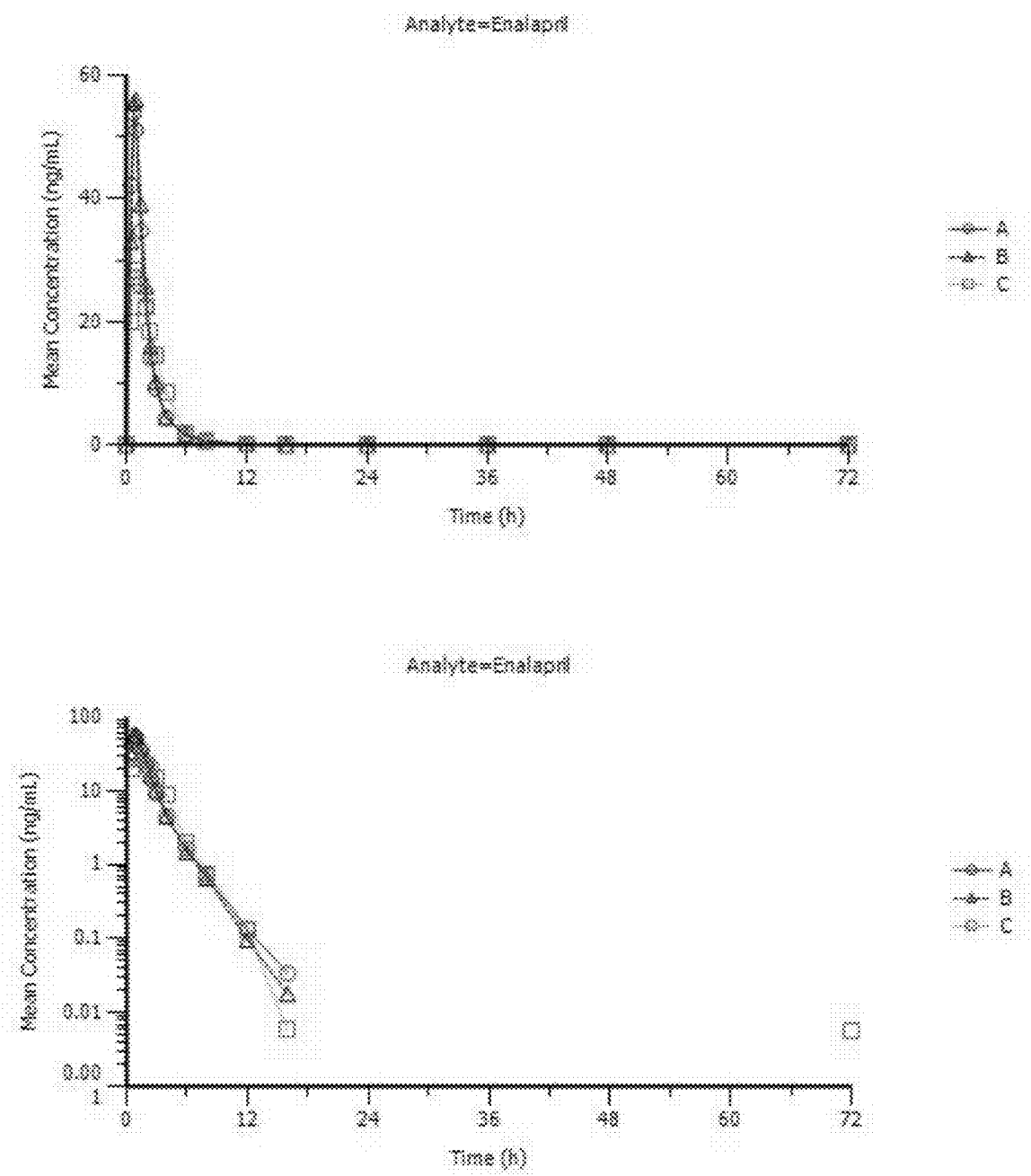
FIG. 3: Mean enalapril concentration-time profiles (linear, top; log, bottom) after administration of test formulation—fasted (Treatment A), reference product—fasted (Treatment B), and test formulation—fed (Treatment C).
Figure 4:
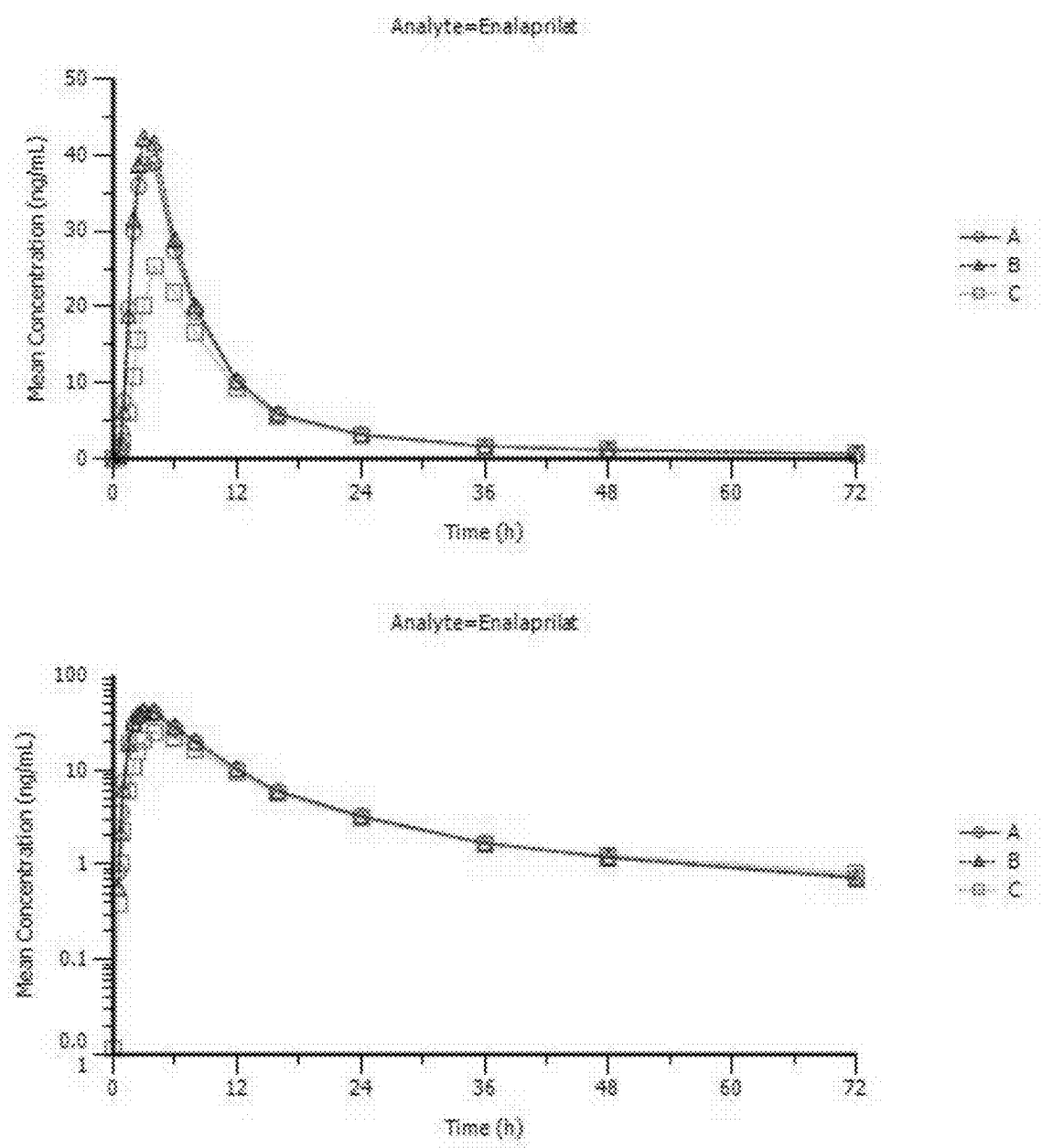
FIG. 4: Mean enalaprilat concentration-time profiles (linear, top; log, bottom) after administration of test formulation—fasted (Treatment A), reference product—fasted (Treatment B), and test formulation—fed (Treatment C).

Concentration-time data are summarized graphically for enalapril in FIG. 3 (linear, top; log, bottom) and enalaprilat in FIG. 4 (linear, top; log, bottom).

Test Formulation Versus Reference Product (Fasted): Based on the geometric mean ratios of enalapril and enalaprilat AUCs (Test/Reference for $AUC_{last}$ and $AUC_{inf}$), the bioavailability of the test formulation relative to the reference product was approximately 96% to 97%. The geometric mean ratios of enalapril and enalaprilat $C_{max}$ were 92.45% and 90.94%, respectively. The 90% confidence intervals about the geometric mean ratios (Test/Reference) of enalapril and enalaprilat $C_{max}$ and AUCs were within the accepted 80% to 125% range, indicating no significant difference.

Test Formulation (Fasted) Versus Test Product (Fed): Based on the geometric mean ratios of enalapril AUCs (Fed/Fasted for $AUC_{last}$ and $AUC_{inf}$), a high-fat meal decreases the bioavailability of enalapril from the test formulation by approximately 14% to 15%; $C_{max}$ is decreased by approximately 46%. For enalaprilat, food decreases $C_{max}$ by approximately 36% and AUCs by approximately 20% to 23%.

Clinical Trial with Mixing Method B: The above trial was conducted with Enalapril maleate oral liquid reconstituted from Enalapril Powder Composition B via Mixing Method A (shake vigorously). The study was discontinued prior to dosing after it was observed that the mixing method created entrapped air bubbles in the liquid and could result in uneven dosing via dosing syringes.

Clinical Trial with Mixing Method B: The above trial was conducted with Enalapril maleate oral liquid reconstituted from Enalapril Powder Composition B via Mixing Method B (gentle swirling and inversion). A number of subjects on the test product only were observed to have very low enalapril and enalaprilat levels in both fasted and fed test treatments. Based on this observation, the reconstituted enalapril maleate test formulation was assayed and it was determined that the test dose administered was not a 10 mg dose as specified in the study protocol, but was a mean dose of about 1.30 mg. Upon further investigation, it was determined that the low concentration of enalapril in the dose occurred due to the mixing method.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating hypertension or prehypertension in a subject, the method comprising administering to that subject a pharmaceutical powder that is reconstituted into an oral liquid formulation, the powder consisting essentially of:
   (a) enalapril or a pharmaceutically acceptable salt thereof,
   (b) a stability agent, and
   (c) colloidal silicon dioxide,
   wherein, when the powder is reconstituted into an oral liquid, the liquid is homogenous and stable for at least 12 weeks at about 25±5° C. and 55±10% relative humidity.

2. The method of claim 1, wherein the enalapril or pharmaceutically acceptable salt thereof is enalapril maleate.

3. The method of claim 1, wherein the stability agent is lactose, sucrose, or mannitol.

4. The method of claim 1, wherein the powder consists essentially of:
   (a) about 14% (w/w) enalapril or a pharmaceutically acceptable salt thereof,
   (b) about 85% (w/w) of the stability agent, and
   (c) about 1% (w/w) colloidal silicon dioxide.

5. The method of claim 1, wherein the powder consists essentially of about 150 mg enalapril, about 890 mg mannitol, and 10 mg colloidal silicon dioxide.

6. The method of claim 1, wherein the powder is stable for at least six months at ambient, accelerated or refrigerated conditions.

7. The method of claim 1, wherein the hypertension is primary hypertension.

8. The method of claim 1, wherein the hypertension is secondary hypertension.

9. The method of claim 1, wherein the subject has blood pressure values greater than or equal to 140/90 mm Hg.

10. The method of claim 1, wherein the subject has blood pressure values of about 120-139/80-89 mm Hg.

11. The method of claim 1, wherein the subject is an adult.

12. The method of claim 1, wherein the subject is elderly.

13. The method of claim 1, wherein the subject is a child.

14. A method of treating hypertension or prehypertension in a subject, the method comprising administering to that subject a pharmaceutical powder that is reconstituted into an oral liquid formulation, the powder consisting essentially of:
   (a) enalapril or a pharmaceutically acceptable salt thereof,
   (b) mannitol, and
   (c) colloidal silicon dioxide,
   wherein, when the powder is reconstituted into an oral liquid, the liquid is homogenous and stable for at least 12 weeks at about 25±5° C. and 55±10% relative humidity.

15. The method of claim 14, wherein the enalapril or pharmaceutically acceptable salt thereof is enalapril maleate.

16. The method of claim 14, wherein the hypertension is primary hypertension.

17. The method of claim 14, wherein the hypertension is secondary hypertension.

18. The method of claim 14, wherein the subject has blood pressure values greater than or equal to 140/90 mm Hg.

19. The method of claim 14, wherein the subject has blood pressure values of about 120-139/80-89 mm Hg.

20. The method of claim 14, wherein the subject is an adult.

21. The method of claim 14, wherein the subject is elderly.

22. The method of claim 14, wherein the subject is a child.

23. A method of treating heart failure or left ventricular dysfunction in a subject, the method comprising administering to that subject a pharmaceutical powder that is reconstituted into an oral liquid formulation, the powder consisting essentially of:
(a) enalapril or a pharmaceutically acceptable salt thereof,
(b) a stability agent, and
(c) colloidal silicon dioxide,
wherein, when the powder is reconstituted into an oral liquid, the liquid is homogenous and stable for at least 12 weeks at about 25±5° C. and 55±10% relative humidity.

24. The method of claim 23, wherein the enalapril or pharmaceutically acceptable salt thereof is enalapril maleate.

25. The method of claim 23, wherein the stability agent is lactose, sucrose, or mannitol.

26. The method of claim 23, wherein the powder consists essentially of:
(a) about 14% (w/w) enalapril or a pharmaceutically acceptable salt thereof,
(b) about 85% (w/w) of the stability agent, and
(c) about 1% (w/w) colloidal silicon dioxide.

27. The method of claim 23, wherein the powder consists essentially of about 150 mg enalapril, about 890 mg mannitol, and 10 mg colloidal silicon dioxide.

28. The method of claim 23, wherein the powder is stable for at least six months at ambient, accelerated or refrigerated conditions.

29. A method of treating heart failure or left ventricular dysfunction in a subject, the method comprising administering to that subject a pharmaceutical powder that is reconstituted into an oral liquid formulation, the powder consisting essentially of:
(a) enalapril or a pharmaceutically acceptable salt thereof,
(b) mannitol, and
(c) colloidal silicon dioxide,
wherein, when the powder is reconstituted into an oral liquid, the liquid is homogenous and stable for at least 12 weeks at about 25±5° C. and 55±10% relative humidity.

30. The method of claim 29, wherein the enalapril or pharmaceutically acceptable salt thereof is enalapril maleate.

* * * * *